United States Patent
Bartek et al.

(10) Patent No.: US 11,702,711 B2
(45) Date of Patent: Jul. 18, 2023

(54) CONTROLLED PH BIOMASS TREATMENT

(71) Applicant: LUSBIO, INC., San Diego, CA (US)

(72) Inventors: Robert Bartek, Centennial, CO (US); Bahman Rejai, Centennial, CO (US)

(73) Assignee: LUSBIO, INC., San Diego, CA (US)

( * ) Notice: Subject to any disclaimer, the term of this patent is extended or adjusted under 35 U.S.C. 154(b) by 0 days.

(21) Appl. No.: 17/048,512

(22) PCT Filed: Apr. 15, 2019

(86) PCT No.: PCT/US2019/027447
§ 371 (c)(1),
(2) Date: Oct. 16, 2020

(87) PCT Pub. No.: WO2019/204190
PCT Pub. Date: Oct. 24, 2019

(65) Prior Publication Data
US 2021/0155995 A1 May 27, 2021

Related U.S. Application Data

(60) Provisional application No. 62/660,283, filed on Apr. 20, 2018.

(51) Int. Cl.
*B01J 23/745* (2006.01)
*C12P 19/02* (2006.01)
(Continued)

(52) U.S. Cl.
CPC ............. *C13K 1/02* (2013.01); *B01J 23/745* (2013.01); *C12P 19/02* (2013.01); *C12P 39/00* (2013.01); *C13K 13/00* (2013.01); *C12P 2201/00* (2013.01)

(58) Field of Classification Search
CPC ....... C12P 2201/00; C12P 19/02; C12P 39/00; C12P 2203/00; C12P 19/14; C13K 1/02; C13K 13/00; B01J 23/745; Y02E 50/10
(Continued)

(56) References Cited

U.S. PATENT DOCUMENTS 3,939,286 A * 2/1976 Jelks ...................... A23K 10/32
426/312
4,604,215 A * 8/1986 McCorquodale ........ B01J 19/10
210/762
(Continued)

FOREIGN PATENT DOCUMENTS

WO 2010071805 A2 6/2010
WO WO2010129170 A3 11/2010
(Continued)

OTHER PUBLICATIONS

Kindsigo et al., Degradation of lignins by wet oxidation: model water solutions, 2006, Proc. Estonian Acad. Sci. Chem., 55, 3, 132-144 (Year: 2006).*
(Continued)

*Primary Examiner* — Coris Fung
*Assistant Examiner* — Ritu S Shirali
(74) *Attorney, Agent, or Firm* — Mendelsohn Dunleavy, P.C.

(57) ABSTRACT

A method for treating biomass including lignocellulosic polymers. The biomass is treated in a mixture of water with at least one oxidizing agent and steam at a temperature in a range of from about 130° C. to about 220° C. for a period from about 5 seconds to about 10 hours. The pH of the mixture is periodically measured for substantially an entire duration of the treating step. As necessary, based on the
(Continued)

measured pH of the mixture, adjusting the pH of the mixture into a range of from about pH 4.5 to about pH 7.5 by adding a base to the mixture.

21 Claims, 5 Drawing Sheets

(51) Int. Cl.
    *C12P 39/00*     (2006.01)
    *C13K 1/02*     (2006.01)
    *C13K 13/00*     (2006.01)

(58) Field of Classification Search
    USPC .......................................................... 127/37
    See application file for complete search history.

(56) References Cited

U.S. PATENT DOCUMENTS

| | | | |
|---|---|---|---|
| 5,846,787 A * | 12/1998 | Ladisch | C12Y 302/01004 435/99 |
| 5,865,898 A | 2/1999 | Holtzapple et al. | |
| 7,189,306 B2 * | 3/2007 | Gervais | C12P 7/10 162/21 |
| 8,481,642 B2 | 7/2013 | Antonietti et al. | |
| 8,506,716 B2 * | 8/2013 | Ahring | C12P 7/08 127/37 |
| 8,741,632 B2 | 6/2014 | Lee et al. | |
| 2009/0004692 A1 | 1/2009 | Vande Berg et al. | |
| 2009/0098618 A1 * | 4/2009 | Burke | C12P 19/14 435/99 |
| 2010/0059388 A1 | 3/2010 | Clarke et al. | |
| 2010/0063271 A1 | 3/2010 | Allan et al. | |
| 2010/0139913 A1 | 6/2010 | Downey | |
| 2010/0262987 A1 | 10/2010 | Imanilov | |
| 2012/0160658 A1 | 6/2012 | Bartek et al. | |
| 2013/0143290 A1 | 6/2013 | Narendranath | |
| 2014/0309467 A1 | 10/2014 | O'Connor | |
| 2015/0147796 A1 | 5/2015 | Bonde | |
| 2016/0096994 A1 | 4/2016 | Flores, III et al. | |
| 2017/0137579 A1 * | 5/2017 | Rudolf von Rohr | C08H 8/00 |
| 2017/0292133 A1 | 10/2017 | Baets et al. | |

FOREIGN PATENT DOCUMENTS

| | | | |
|---|---|---|---|
| WO | WO2011071533 A1 | 6/2011 | |
| WO | WO-2011112737 A2 * | 9/2011 | ............. C02F 3/006 |
| WO | WO2014185957 A1 | 11/2014 | |
| WO | 2015193243 A1 | 12/2015 | |
| WO | WO-2016130494 A1 * | 8/2016 | ............. C10G 1/06 |
| WO | 2019204192 A1 | 10/2019 | |

OTHER PUBLICATIONS

The Engineering Tool Box: Water—Saturation Pressure [online], [retrieved on Jan. 12, 2022], Retrieved from the internet: <URL: https://www.engineeringtoolbox.com/water-vapor-saturation-pressure-d_599.html> (Year: 2022).*

Bhadha et al., Bagasse: A Potential Organic Soil Amendment Used in Sugarcane Production, Aug. 2020, UF/IFAS Extension, pp. 1-5 (Year: 2020).*

Adelaide: What does ppm mean [online], [retrieved on Jan. 15, 2022], Retrieved from the internet: <URL: https://www.adelaide.edu.au/arcpoh/dperu/fluoride/ppm.html> (Year: 2022).*

Weil et al., Continuous pH Monitoring During Pretreatment of Yellow Poplar Wood Sawdust by Pressure Cooking in Water, 1998, Applied Biochemistry and Biotechnology, vol. 70-72, pp. 99-111 (Year: 1998).*

Kim et al., Chapter 6: Pretreatment of Biomass by Aqueous Ammonia for Bioethanol Production, 2009, Biofuels: Methods and Protocols, Methods in Molecular Biology, vol. 581, pp. 79-91 (Year: 2009).*

Rehman et al., Structure-function relationship of extremozymes, 2022, Microbial Extremozymes: Novel Sources and Industrial Applications, pp. 9-30. Retrieved from the internet < URL: https://www.sciencedirect.com/topics/agricultural-and-biological-sciences/xylanases> (Year: 2022).*

Bjerre et al., Pretreatment of Wheat Straw using Combined Wet Oxidation and Alkaline Hydrolysis Resulting in Convertible Cellulose and Hemicellulose, 1996, Biotechnology and Bioengineering, vol. 49, p. 568-577 (Year: 1996).*

Demesa et al., Alkaline Partial Wet Oxidation of Lignin for the Production of Carboxylic Acids, 2015, Chem. Eng. Technol., vol. 38, No. 12, 2270-2278 (Year: 2015).*

Jennings et al., Conditioning of dilute-acid pretreated corn stover hydrolysate liquors by treatment with lime or ammonium hydroxide to improve conversion of sugars to ethanol, 2011, Bioresource Technology, 102, pp. 1240-1245 (Year: 2011).*

Biology Dictionary: Fermentation [online], [retrieved on Aug. 5, 2022], Retrieved from the internet: < URL: https://biologydictionary.net/fermentation/> (Year: 2022).*

International Search Report and Written Opinion for corresponding International application No. PCT/US2019/027447 dated Aug. 7, 2019 (9 pages).

Bridgewater, Anthony V. "Review of fast pyrolysis of biomass and product upgrading." Biomass and Bioenergy 38 (2012): 68-94.

McMillan, J. D., "Processes for pretreating lignocellulosic biomass: A Review" No. NREL/TP-421/4978. National Renewable Energy Lab., Golden, CO (United States), (1992): 48 pages.

Kelkar, Shantanu, et al. "Pyrolysis of spent coffee grounds using a screw-conveyor reactor" Fuel Processing Technology 137 (2015): 170-178.

Sasaki, Mitsuru, et al. "Cellulose hydrolysis in subcritical and supercritical water." The Journal of Supercritical Fluids 13 (1998): 261-268.

Martinez, Diego, et al. "Genome, transcriptome, and secretome analysis of wood decay fungus Postia placenta supports unique mechanisms of lignocellulose conversion." Proceedings of the National Academy of Sciences 106.6 (2009): 1954-1959.

Saka, Shiro, et al. "Chemical conversion of various celluloses to glucose and its derivatives in supercritical water." Cellulose 6.3 (1999): 177-191.

Wymelenberg, Amber Vanden, et al. "Comparative Transcriptome and Secretome Analysis of Wood Decay Fungi Postia placenta and Phanerochaete chrysosporium." Applied and Environmental Microbiology 76.11 (2010) 3599-3610.

Extended European Search Report and Written Opinion for corresponding European application No. 19789399.3, dated Apr. 25, 2022 (11 pages).

* cited by examiner

CONTROLLED PH BIOMASS TREATMENT

FIELD OF THE INVENTION

The present invention relates to conversion of biomass to sugars and other small organic compounds. In particular, the present invention is directed to oxidation of the biomass in a controlled pH environment at a low temperature and a low pressure to increase the production of sugars and other small organic compounds.

DESCRIPTION OF THE RELATED TECHNOLOGY

Energy, together with carbon dioxide and water, is trapped in trees and other plants by conversion into organic compounds, collectively called biomass. Many types of biomass, including, for example, wood, paper, agricultural residues such as bagasse, switchgrass, wheat or sorghum straw, corn husks, and the like have long been considered as possible feedstocks for the manufacture of organic chemicals or biofuels.

The major components, typically about 60 wt. % to 80 wt. %, of biomass are polysaccharides (e.g., cellulose and hemicellulose). Another major component of biomass, typically making up about 15 wt. % to 25 wt. % is lignin. Cellulose is one of the most abundant natural resources available. The cellulose, hemicellulose and lignin are bound together in biomass, together with smaller amounts of pectins, proteins, and minerals.

The energy trapped within the biomass can be recovered, in part, by breaking down the polysaccharides into their constituent sugars, which may be, for example, subsequently converted to ethanol by fermentation. In addition, breakdown of lignin can yield aromatic compounds for incorporation into diesel fuel. The challenge is how to achieve these results by treatment of biomass in a large-scale, commercially practical, and energy efficient way.

It is believed by many that due to the structure of most biomass, microorganisms and enzymes cannot effectively attack the cellulose, without pre-treatment of the biomass. Conventional methods for converting cellulose to glucose by way of acid hydrolysis and enzymatic saccharification are known to be inefficient and, consequently, are not commercially viable.

More recently, chemical conversion of cellulose with supercritical water to obtain various sugars has been studied. (see, e.g., M. Sasaki, B. Kabyemela, R. Malaluan, S. Hirose, N. Takeda, T. Adschiri & K. Arai, "Cellulose hydrolysis in subcritical and supercritical water", *J. Supercritical Fluids*, 13, 261-268 (1998); S. Saki & T. Ueno, "Chemical conversion of celluloses to glucose and its derivatives in supercritical water", *Cellulose*, 6, 177-191 (1999).) These studies demonstrate that cellulose may be rapidly hydrolyzed in supercritical water to provide relatively high yields of glucose in flow or batch type micro-reactors. The use of these small scale flow or batch type micro-reactors is not a realistic option for commercial-scale conversion of biomass to useful chemicals and biofuels.

US 2010/0063271 discloses a method for converting biomass materials into reaction products including fermentable sugars and various aromatics. The method includes steps of: extruding a mixture of a biomass material and water into a supercritical fluid biomass conversion zone; heating and pressurizing the mixture to yield supercritical water; retaining the mixture for a period of time sufficient to yield the reaction products; and separating the reaction products by solvent fractionation. The conditions used in the supercritical fluid biomass conversion zone of this method, however, are so severe that a significant amount of biomass is converted to undesirable carbon dioxide.

U.S. Pat. No. 8,741,632 discloses a method for treatment of biomass using a combination of mechanical, chemical and thermal effects (i.e., nano-hybrid treatment) to synergistically break down the biomass structures for enhancing enzymatic accessibility to lignocellulosic materials. The biomass is nanomixed with a fluid in a turbine nanomixer to form break down the biomass and open pores to allow access by enzymes. This process consumes a large amount of energy, thus is not commercially viable.

US 2014/0309467 discloses a catalytic system for pyrolysis of a solid biomass material. Pyrolysis is the thermal decomposition of biomass in the absence of oxygen (see Bridgwater, Review of fast pyrolysis of biomass and product upgrading, *Biomass and Bioenergy*, vol. 38, pp. 68-94, 2012). The catalytic system can be an inorganic carbonate and/or an inorganic hydrogen carbonate. The product of pyrolysis is bio-oil or bio-crude that can be used as a hydrocarbon fuel.

WO 2010/129170 discloses another pyrolysis method for converting solid biomass to gaseous and liquid products. The biomass is mixed with a cool particulate heat transfer material that may have catalytic properties, followed by fluidizing the mixture and then feeding the mixture into the pyrolysis reactor. In the reactor, the biomass material is heated and converted into the final product. Pyrolysis processes are generally less efficient than thermochemical processes involving oxidizing agents.

U.S. Pat. No. 8,481,642 discloses a process for converting biomass to a coal-like hybrid material by heating of a reaction mixture of water, biomass and a copolymerizable compound. The biomass is first converted to activated biomass and then copolymerized with a polymerization initiator. By selecting different copolymerizable compounds, e.g. petrochemical compounds the physical properties of the products and the preparation process thereof can be controlled. The conversion rate of this process is low as cellulose inside of the biomass particles typically remains inaccessible.

WO 2014/185957 discloses a method for treating a carbonaceous feedstock, especially coal, by heating with a solubilizing agent and water in the presence of an oxidizing agent to a temperature below 300° C. and a pressure below 1230 psig. The mild conditions oxidatively depolymerize the carbonaceous feedstock and enhance the biodegradability of the resulting mixture to chemicals and biogas. The mild conditions ensure less loss of carbon to $CO_2$. However, the cellulose inside of the carbonaceous feedstock typically remains inaccessible and thus the conversion of this process can be improved.

Many prior art processes convert only a fraction of the total carbon in biomass to desired products. One major limitation is that the fermentable or digestible cellulose and hemicellulose deep inside of the biomass is not easily accessible to the microorganisms or enzymes used in these processes because the lignin component may link the cellulose/hemicellulose into a tight crystalline structure. Disruption of lignin can change the crystalline structure and make the cellulose/hemicellulose more accessible. Unfortunately, processes that disrupt lignin in the biomass, typically also convert a large portion of cellulose/hemicellulose in the biomass into undesirable $CO_2$. Alternatively, if relatively mild conditions are employed, significantly less lignin is disrupted but a significant portion of cellulose/hemicellulose inside of the biomass remains inaccessible.

The present invention addresses these problems by providing a treatment process using mild conditions designed to preferentially disrupt lignin in the biomass while preserving cellulose/hemicellulose for downstream enzymatic treatment or fermentation by microorganisms. The pH is controlled during the process using a base. By disrupting a large amount of lignin while preserving the cellulose/hemicellulose in the biomass, the present invention significantly enhances the yield of sugars and other small organic compounds obtainable from biomass.

SUMMARY OF THE INVENTION

In one aspect, the present invention provides a method for treating biomass including lignocellulosic polymers. The method includes steps of:

(a) treating a mixture of the biomass and water, with at least one oxidizing agent and steam, at a temperature in a range of from about 130° C. to about 220° C. for a period of from about 5 seconds to about 10 hours;

(b) periodically measuring a pH of the mixture for substantially an entire duration of step (a); and (c) as necessary, based on the pH of the mixture measured in step (b), adjusting the pH of the mixture into a range of from about pH 4.5 to about pH 7.5 by adding a base to the mixture.

In the previous embodiment, the biomass may be selected from agricultural wastes, wood wastes and gardening wastes, or the biomass may be selected from corn stover, corn cobs, palm tree empty fruit bunches, sugar cane bagasse, straw from grain crops, hay, wood waste from thinnings of deciduous and conifer forestry, sawdust from lumbering and furniture making, guayule residuals after natural rubber extraction, waste paper and cardboard. In one embodiment solid waste from the pulp & paper industry may be treated by the method of the invention.

In each of the previous embodiments, the at least one oxidizing agent may be selected from air, oxygen enriched air, oxygen, ozone, perchlorates, carbon dioxide, nitrous oxide, oxides, superoxides, permanganates, chlorates, peroxides, hypochlorites and nitrates.

In each of the previous embodiments, the weight ratio of the oxygen introduced by the at least one oxidizing agent to the carbon in the biomass may be in a range of from about 0.2 to about 1.0, or from about 0.3 to about 0.9, or from about 0.3 to about 0.8, or from about 0.4 to about 0.7, or from about 0.4 to about 0.6, or from about 0.5 to about 0.6.

In each of the previous embodiments, the range for the pH of the mixture may be from about 4.5 to about 7.0, or from about 4.5 to about 6.5, or from about 4.5 to about 6.0, or from about 4.5 to about 5.5, or from about 5.5 to about 7.5, or from about 5.5 to about 7.0, or from about 6.0 to about 7.0, or from about 6.0 to about 6.5.

In each of the previous embodiments, the pH of the mixture may be measured every second, 5 seconds, 10 seconds, 20 seconds, 30 seconds, 45 seconds, minute, 2 minutes, 4 minutes, 6 minutes, 8 minutes, 10 minutes, 15 minutes, 20 minutes, 30 minutes or every hour.

In each of the previous embodiments, the base may be selected from oxides, hydroxides, carbonates, bicarbonates, urea, borates, and halogenates of Group I and Group II elements, ammonia, ammonium hydroxide, urea and combinations thereof.

In each of the previous embodiments, the amount of base added to the mixture may be in the range of from about 1 to about 10 wt. %, or from about 1 to about 9 wt. %, or from about 2 to about 9 wt. %, or from about 2 to about 8 wt. %, or from about 2 to about 7 wt. %, or from about 3 to about 7 wt. %, or from about 3 to about 6 wt. %, or from about 4 to about 6 wt. %, based on the dry weight of the biomass.

In each of the previous embodiments, the amount of steam employed may be from about 0.1 to about 5.0 wt. %, or from about 0.5 to about 4.0 wt. %, or from about 1.0 to about 3.0 wt. %, based on a dry weight of the biomass.

In each of the previous embodiments, the steam may be generated in situ from the moisture in the biomass and/or water in the mixture.

In each of the previous embodiments, the temperature may be in a range of from about 130° C. to about 210° C., or from about 140° C. to about 210° C., or from about 140° C. to about 200° C., or from about 150° C. to about 200° C., or from about 150° C. to about 190° C., or from about 150° C. to about 180° C., or from about 160° C. to about 180° C., or from about 160° C. to about 170° C.

In each of the previous embodiments, the treatment process may be performed under a pressure in a range of from about 201.3 KPa to about 2068 KPa, or from about 239.2 KPa to about 1724 KPa, or from about 239.2 KPa to about 1379 KPa, or from about 308.2 KPa to about 928.7 KPa, or from about 308.2 KPa to about 790.8 KPa, or from about 308.2 KPa to about 721.9 KPa, or from about 308.2 KPa to about 652.9 KPa, or from about 308.2 KPa to about 584.0 KPa, or from about 308.2 KPa to about 515.0 KPa, or from about 308.2 KPa to about 446.1 KPa, or from about 308.2 KPa to about 377.1 KPa.

In each of the previous embodiments, the duration of the treatment process may be from about 10 seconds to about 9 hours, or from about 20 seconds to about 8 hours, or from about 30 seconds to about 8 hours, or from about 45 seconds to about 8 hours, or from about 1 minute to about 7 hours, or from about 2 minutes to about 7 hours, or from about 5 minutes to about 7 hours, or from about 10 minutes to about 6 hours, or from 15 about minutes to about 6 hours, or from about 20 minutes to about 6 hours, or from about 30 minutes to about 5 hours, or from about 5 seconds to about 1 hour, or from about 10 seconds to about 55 minutes, or from about 20 seconds to about 55 minutes, or from about 30 seconds to about 55 minutes, or from about 45 seconds to about 50 minutes, or from about 1 minute to about 50 minutes, or from 2 about minutes to about 50 minutes, or from about 5 minutes to about 50 minutes, or from about 10 minutes to about 40 minutes, or from about 15 minutes to about 40 minutes, or from about 15 minutes to about 30 minutes, or from about 1 hour to about 10 hours, or from about 1 hour to about 9 hours, or from about 1 hour to about 8 hours, or from about 1 hour to about 7 hours, or from about 1 hour to about 6 hours, or from about 1 hour to about 5 hours, or from about 1 hour to about 4 hours, or from about 1.5 hours to about 4 hours, or from about 1.5 hours to about 3 hours, or from about 1.5 hours to about 2.5 hours.

In each of the previous embodiments, the treatment process may have a severity factor in the range of from about 2.5 to about 4.5, or from about 2.7 to about 4.3, or from about 2.9 to about 4.1, or from about 3.0 to about 4.0, or from about 3.2 to about 4.0, or from about 3.2 to about 3.8, or from about 3.3 to about 3.7, or from about 3.4 to about 3.6.

In each of the previous embodiments, the mixture may further include an oxidation catalyst. The oxidation catalyst may be selected from water insoluble metals, transition metals, precious metals, their salts or oxides, and combinations thereof or the oxidation catalyst may include a metal selected from nickel, cobalt, platinum, palladium, rhenium, iron, copper, vanadium, zirconium and ruthenium. The oxidation catalyst may be supported on inert substrate selected from clay, alumina, silica, silica alumina, zeolites, activated carbon, diatomaceous earth, titania, zirconia, molybdena, ceramics, and combinations thereof.

In each of the previous embodiments, the method may further include a step of preprocessing the biomass selected from grinding, milling and crushing the biomass. The preprocessing step may reduce the biomass to pieces or chips 12 cm or less in length particles or slices or stripes, having an average size of from 0.2 mm to 12 cm, or 1-10 cm, or from 2 to 8 cm. In one embodiment, the preprocessed mass has straw-like dimension with length of from 2 cm to 8 cm, or from 3 to 6 cm.

In each of the previous embodiments, the method may further include a step selected from enzymatic treatment of the oxidation products and fermentation of the oxidation products. The enzymatic treatment of the oxidation products may employ at least one enzyme selected from xylanases, cellulases, hemicellulases, xylosidase, esterase, arabinofuranosidase, galactanase, oxidases, peroxidases, mannases, laccases, oxidoreductases, pectinases and lipases. The enzyme may be introduced by addition of an organism capable of producing and excreting such enzymes. The fermentation of the oxidation product may use one or more of bacteria, yeasts and fungi and may be carried in a microbial digester. The fermentation may be selected from an aerobic process, an anaerobic process, and a combination of aerobic and anaerobic processes.

In each of the previous embodiments, the method may further include a step of using one or more of the oxidation products for agricultural applications. These agricultural applications may include using the product(s) in a growing medium or a fertilizer.

DETAILED DESCRIPTION OF THE PREFERRED EMBODIMENT(S)

Figure 1:
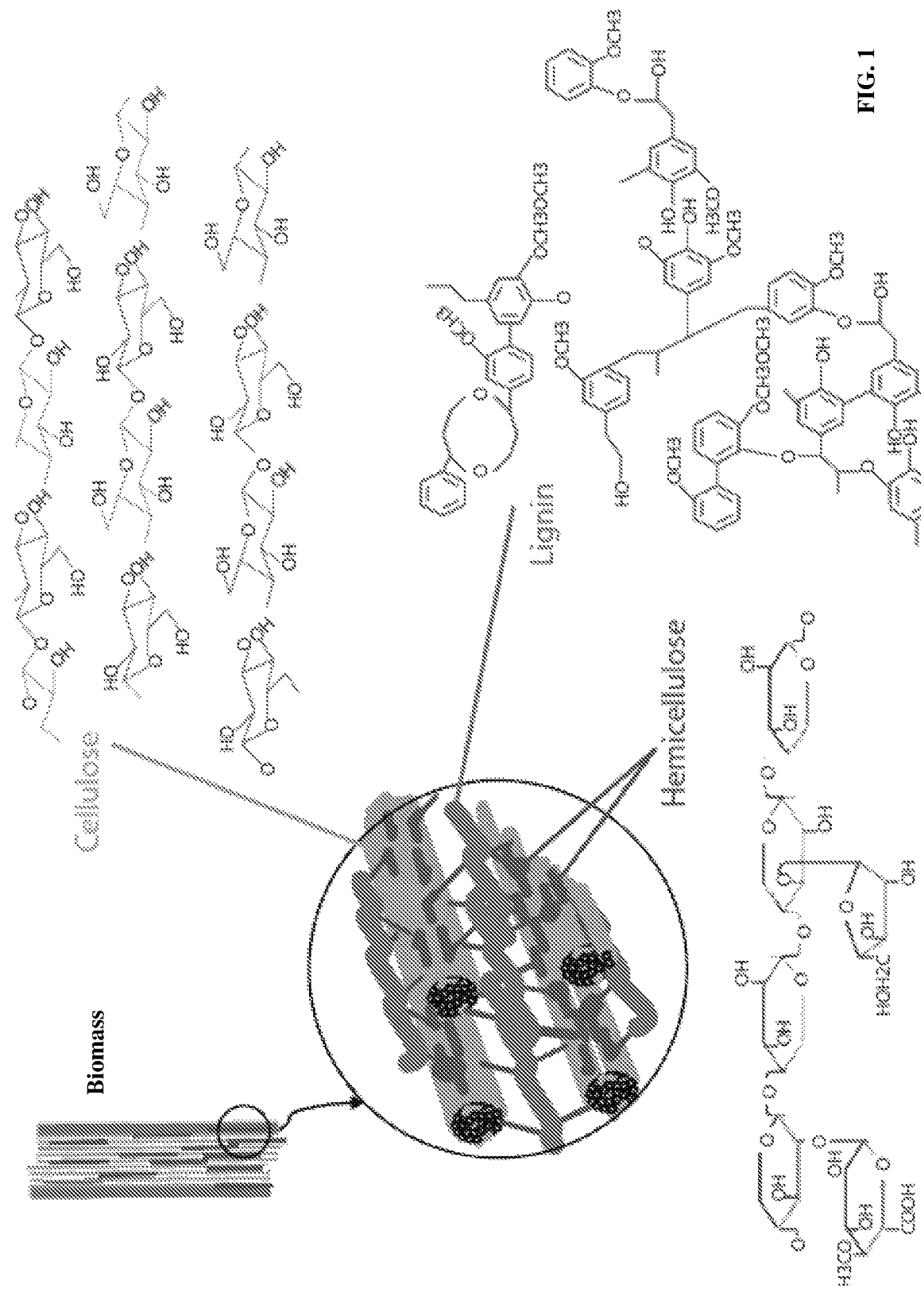
FIG. 1 is a diagram depicting the structure of biomass with lignin linking cellulose and hemicellulose into a compact structure, which makes it difficult for enzymes or microorganisms to access the cellulose and hemicellulose.

For illustrative purposes, the principles of the present invention are described by referencing various exemplary embodiments. Although certain embodiments of the invention are specifically described herein, one of ordinary skill in the art will readily recognize that the same principles are equally applicable to, and can be employed in other systems and methods. Before explaining the disclosed embodiments of the present invention in detail, it is to be understood that the invention is not limited in its application to the details of any particular embodiment shown. Additionally, the terminology used herein is for the purpose of description and not of limitation. Furthermore, although certain methods are described with reference to steps that are presented herein in a certain order, in many instances, these steps may be performed in any order as may be appreciated by one skilled in the art; the novel method is therefore not limited to the particular arrangement of steps disclosed herein.

It must be noted that as used herein and in the appended claims, the singular forms "a", "an", and "the" include plural references unless the context clearly dictates otherwise. Furthermore, the terms "a" (or "an"), "one or more" and "at least one" can be used interchangeably herein. The terms "comprising", "including", "having" and "constructed from" can also be used interchangeably.

Unless otherwise indicated, all numbers expressing quantities of ingredients, properties such as molecular weight, percent, ratio, reaction conditions, and so forth used in the specification are to be understood as being modified in all instances by the term "about," whether or not the term "about" is present. Accordingly, unless indicated to the contrary, the numerical parameters set forth in the specification are approximations that may vary depending upon the desired properties sought to be obtained by the present disclosure. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in their respective testing measurements.

It is to be understood that each component, compound, substituent or parameter disclosed herein is to be interpreted as being disclosed for use alone or in combination with one or more of each and every other component, compound, substituent or parameter disclosed herein.

It is also to be understood that each amount/value or range of amounts/values for each component, compound, substituent or parameter disclosed herein is to be interpreted as also being disclosed in combination with each amount/value or range of amounts/values disclosed for any other component(s), compounds(s), substituent(s) or parameter(s) disclosed herein and that any combination of amounts/values or ranges of amounts/values for two or more component(s), compounds(s), substituent(s) or parameters disclosed herein are thus also disclosed in combination with each other for the purposes of this description.

It is further understood that each range disclosed herein is to be interpreted as a disclosure of each specific value within the disclosed range that has the same number of significant digits. Thus, a range of from 1-4 is to be interpreted as an express disclosure of the values 1, 2, 3 and 4. It is further understood that each lower limit of each range disclosed herein is to be interpreted as disclosed in combination with each upper limit of each range and each specific value within each range disclosed herein for the same component, compounds, substituent or parameter. Thus, this disclosure to be interpreted as a disclosure of all ranges derived by combining each lower limit of each range with each upper limit of each range or with each specific value within each range, or by combining each upper limit of each range with each specific value within each range.

Furthermore, specific amounts/values of a component, compound, substituent or parameter disclosed in the description, including the examples, is to be interpreted as a disclosure of either a lower or an upper limit of a range and thus can be combined with any other lower or upper limit of a range or specific amount/value for the same component, compound, substituent or parameter disclosed elsewhere in the application to form a range for that component, compound, substituent or parameter.

The terms "biomass" and "lignocellulosic biomass" are used interchangeably and refer to plant-derived organic matter (woody or non-woody) that contains lignocellulosic polymers. Examples of biomass can include, but are not limited to, agricultural crop wastes and residues such as corn stover, wheat straw, rice straw, soybean straw, sorghum straw, barley straw, oat straw, rye straw, herbs, legumes, straw of short rotation herbaceous crops such as switchgrass, alfalfa, and so forth, sugar cane bagasse, tobacco, and various weeds of any type, such as in the Bassicacae family (e.g., *Arabidopsis*), woody energy crops, wood wastes and residues such as trees (e.g., dogwood), including fruit-bearing trees, (e.g., apple trees, orange trees, and the like), softwood forest thinnings, barky wastes, sawdust, paper and pulp industry waste streams, wood fiber, and the like. Additional grass crops, such as various prairie grasses, including prairie cord grass, switchgrass, big bluestem, little bluestem, sideoats grama, and the like, have potential to be produced large-scale as additional plant biomass sources. For urban areas, potential plant biomass includes yard waste (e.g., grass clippings, leaves, tree clippings, brush, etc.) and vegetable processing waste.

In some embodiments, the biomass is a non-food source of waste lignocellulosic biomass, in particular leftover materials from agriculture, forestry, and the like. Specific examples include corn stover, corn cobs, empty fruit bunches of palm trees, sugar cane bagasse, straw from grain operations, wood waste from thinnings of deciduous (poplar, maple) and conifer forestry (southern yellow pine, Douglas fir), sawdust from lumbering and furniture making, guayule residuals after natural rubber extraction, and even waste paper and cardboard from municipal solid waste. In another embodiment, the biomass contains "energy grasses", which are grown for the purpose of being converted to biofuel.

The term "cellulose" as used herein refers to a natural carbohydrate, high molecular weight polymer, e.g., polysaccharide, including anhydroglucose units joined by an oxygen linkage to form long molecular chains that are essentially linear. The degree of polymerization can be about 1,000 monomer units for wood pulp to about 3,500 monomer units for cotton fiber with a molecular weight of about 160,000 g/mol to about 560,000 g/mol.

The term "hemicellulose" as used herein refers a polymer component of biomass that contains sugar monomers other than glucose, in contrast to cellulose, which contains only glucose. Hemicelluloses contain D-pentose sugars, and occasionally small amounts of L-sugars. In addition to glucose, hemicellulose may include xylose, mannose, galactose, rhamnose, and arabinose, with xylose being the most common sugar monomer. The sugars in hemicellulose may be linked by ester linkages as well as glycosidic linkages. Exemplary forms of hemicellulose include galactan, mannan, xylan, arabanan, arabinoxylan, glucomannan, and galactomanan.

The term "lignin" as used herein means a phenolic polymer of amorphous structure including about 17% to about 30%, by weight, of wood. Lignin is associated with cellulose and hemicellulose polymers that can make up most of the balance of the biomass. Generally, it is believed that lignin serves as a binder of cellulose and hemicellulose in biomass.

The term "lignocellulosic polymer" as used herein refers lignin, cellulose and hemicellulose polymers, where the lignin binds the cellulose and hemicellulose in a tight network (FIG. 1). Lignocellulosic polymers are a major component of the biomass. There are also lesser amounts of other compounds in the biomass, such as proteins, long chain fatty acids, salts, and minerals. In one example, the lignocellulosic polymers contain 11-25 wt. % of lignin, 8-40 wt. % of hemicellulose, and 30-57 wt. % of cellulose.

As used herein, the term "microorganism" includes bacteria, archaea and fungi. The microorganisms may include, for example, Archaeoglobales, Thermotogales, *Cytophaga* group, *Azospirillum* group, *Paracoccus* subgroup, *Sphingomonas* group, *Nitrosomonas* group, *Azoarcus* group, *Acidovorax* subgroup, *Oxalobacter* group, *Thiobacillus* group, *Xanthomonas* group, *Oceanospirillum* group, *Pseudomonas* and relatives, *Marinobacter hydrocarbonoclaticus* group, *Pseudoalteromonas* group, *Vibrio* subgroup, *Aeromonas* group, *Desulfovibrio* group, *Desulfuromonas* group, *Desulfobulbus* assemblage, *Campylobacter* group, *Acidimicrobium* group, *Frankia* subgroup, *Arthrobacter* and relatives, *Nocardiodes* subgroup, *Thermoanaerobacter* and relatives, *Bacillus megaterium* group, *Carnobacterium* group, *Clostridium* and relatives, and archaea such as Methanobacteriales, Methanomicrobacteria and relatives, Methanopyrales, and Methanococcales.

More specific examples of microorganisms may include, for example, *Aerobacter, Aeromonas, Alcaligenes, Bacillus, Bacteroides, Clostridium, Escherichia, Klebsiella, Leptospira, Micrococcus, Neisseria, Paracolobacterium, Proteus, Pseudomonas, Rhodopseudomonas, Sarcina, Serratia, Streptococcus* and *Streptomyces,* Methanobacterium omelianskii, Mb. Formicium, Mb. Sohngenii, Methanosarcina barkeri, Ms. Methanica, Mc. Masei, Methanobacterium thermoautotrophicum, Methanobacterium bryantii, Methanobrevibacter smithii, Methanobrevibacter arboriphilus, Methanobrevibacter ruminantium, Methanospirillum hungatei, Methanococcus vannielli, Methanothrix soehngenii, Methanothrix sp., Methanosarcina mazei, Methanosarcina thermophila, Methanobacteriaceae, Methanosarcinaceae, Methanosaetaceae, Methanocorpusculaceae, Methaanomicrobiaceae, other archaea and any combination of these.

The term "treatment step" or "treating" as used herein refers to a step or process intended to alter the native biomass structure such that it can be more efficiently and economically used in a downstream process, including fermentation, agricultural uses or enzymatic conversion to chemical compounds, such as small molecule sugars, alcohols (methanol, ethanol, propanols, etc.), and small molecule hydrocarbons (methane, ethane, propane, etc.). Treatment can reduce the degree of crystallinity of lignocellulose polymers in the biomass, reduce the interference of lignin with biomass conversion and prehydrolyze some of the structural carbohydrates, thus increasing their enzymatic digestibility and/or microorganism accessibility.

The term "substantially" as used herein means an amount of at least generally about 80%, alternatively at least about 90%, alternatively at least about 95%, or alternatively at least about 99%.

In one aspect, the present invention provides a treatment method for treating biomass that contains lignocellulosic polymers. The method includes the steps of:

(a) treating a mixture of the biomass and water, with at least one oxidizing agent and steam, at a temperature in a range of from about 130° C. to about 220° C. for a period from about 5 seconds to about 10 hours; and (b) periodically measuring the pH of the mixture for substantially an entire duration of step (a), and, (c) as necessary, based on the pH measured in step (b) adjusting the pH of the mixture into a range of from about pH 4.5 to about pH 7.5 by adding a base to the mixture. In a preferred embodiment, the pH of the mixture is maintained in the range of from about pH 4.5 to about pH 7.5 for substantially the entire duration of step (a).

The treatment process is designed to preferentially degrade the lignin as much as possible while preserving as much cellulose/hemicellulose for downstream use or treatment with enzymes and/or microorganisms to produce small molecule sugars, alcohols (methanol, ethanol, propanol, etc.), and small molecule hydrocarbons (methane, ethane, propane, etc.), etc., or to be used in agricultural applications as fertilizers or bases of growing compost or growing medium to produce food products.

The treatment method of the present invention preferentially degrades the lignin in the biomass while preserving the cellulose and hemicellulose by controlling the pH during the treatment process to be in the range of from about 4.5 to about 7.5. Treatment in this pH range using steam and an oxidizing agent preferentially oxidizes lignin rather than the cellulose and hemicellulose in the biomass.

The treatment process uses at least one oxidizing agent to oxidize lignin, which produces carboxylic acids and $CO_2$. The produced $CO_2$ will dissolve in the treatment mixture to become carbonic acid which, together with the carboxylic acids, lower the pH of the mixture. Without pH adjustment, the pH may drop as low as 2, which provides conditions more suitable for hydrolysis of hemicellulose, and, to a lesser extent, cellulose. Further, a pH below 4.5 may also favor secondary repolymerization reactions of intermediates resulting from oxidization/hydrolysis of lignin, cellulose and hemicellulose, and other material breakdown, to thereby form larger, more bio-recalcitrant polymers that are more inert than the lignocellulosic materials.

In the present process, the pH of the treatment mixture is periodically monitored and, as necessary, adjusted to be in the range of about pH 4.5 to about pH 7.5. In some embodiments, such as when the treatment product is intended for downstream enzymatic treatment, it may be desirable to maintain the pH in the range of from about pH 4.5 to about pH 7.0, or from about pH 4.5 to about pH 6.5, or from about pH 4.5 to about pH 6.0, or from about pH 4.5 to about pH 5.5. In some other embodiments, when the treatment product is intended for downstream fermentation or agricultural applications, it may be desirable to maintain the pH in the range of from about pH 5.5 to about pH 7.5, or from about pH 5.5 to about pH 7.0, or from about pH 6.0 to about pH 7.0, or from about pH 6.0 to about pH 6.5.

The pH of the treatment mixture is monitored during the substantially the entire duration of the treatment process. As necessary, based on the measured pH value, the pH is adjusted by adding a base to the mixture. For example, the pH of the mixture may be measured continuously, or at least about 2 times, or about 5 times, or about 10 times, or about 20 times, or about 30 times, or about 40 times, or about 50 times, or about 60 times, or about 80 times, or about 100 times during the treatment process. Preferably, the pH is measured continuously or at regular time intervals, i.e. periodically.

Depending on the duration of the treatment process, pH measurements may be carried out, for example, once every second, or every about 5 seconds, or every about 10 seconds, or every about 20 seconds, or every about 30 seconds, or about 45 seconds, or every about 1 minute, or every about 2 minutes, or every about 4 minutes, or every about 6 minutes, or every about 8 minutes, or every about 10 minutes, or every about 15 minutes, or every about 20 minutes, or every about 30 minutes, or every about 1 hour.

Once the pH in the treatment mixture is measured to be lower than or approaching the lower bound of the desired pH range, a base is added to the treatment mixture to titrate acids in the mixture to adjust the pH into the desired pH range. Titration techniques well-known in the art may be employed in the treatment process. Such titration techniques may involve slowly adding the base and monitoring the pH at the same time until the pH is adjusted into the desired pH range.

Suitable bases for use in the treatment process include mineral bases, such as oxides, hydroxides, carbonates, borates and halogenates of Group I and Group II elements, i.e. alkali metals and alkaline earth metals, respectively, as well as ammonia, ammonium hydroxide, urea, or other forms of nitrogen that can form hydroxyl groups when dissolved in water. Examples of suitable metals include sodium, potassium, calcium, and magnesium compounds. Naturally occurring materials including these bases may also be used in this process. These include, but are not limited to Nahcolite, Trona, Thermonatrite, Gaylussite, Hydromagnesite, Lansfordite, Ikaite, Hydrocalcite, Dolomite, Huntite, Aragonite, Natrite, Magnesite, Calcite, Kalcinite, Gregoryite, and others. Examples of suitable bases include sodium hydroxide, potassium hydroxide, ammonium hydroxide, sodium carbonate, sodium bicarbonate and potassium carbonate, or any mixture of these. Other bases found in biological systems may also be used, including ammonia, ammonium hydroxide, urea, or other forms of nitrogen that can form hydroxyl groups when dissolved in water.

In one embodiment, the base is selected such that the base does not add to the soluble mineral burden of the treatment product, which can affect downstream treatment. Thus, the base may be selected from, for example, ammonium hydroxide and urea that are free of minerals. Further, ammonia gas may be used.

The amount of base used in the treatment process may depend on the type and age of the biomass, desired severity of the treatment, the type of base and the targeted pH during the treatment process. As an example, for a typical corn stover biomass, to control the pH of the treatment mixture to be about pH 5, the amount of sodium hydroxide required may range from about 5.5 to about 6.5 wt. % of the total weight of the corn stover under typical treatment conditions. If the pH of the treatment mixture is controlled to be about pH 4, the amount of sodium hydroxide required is about 15% less, i.e., from about 4.7 to about 5.5 wt. % of the total weight of the corn stover. If ammonium hydroxide is used to adjust the pH, the amount of base needed, by weight, will be about 12% less than when using sodium hydroxide under similar treatment conditions.

In some embodiments, a certain amount of base may be added to the treatment mixture before the start of the treatment process. Treatment may be carried out in batch mode or continuous mode. When treatment is carried out as a batch process, the amount of base that is required can be estimated based on prior knowledge/experience. At least a portion of, or all of, the estimated amount of the base may be added before the start of the treatment process. In a continuous process, base is added as dictated by the need to adjust the pH of the treatment mixture into the desired range as the process proceeds.

Base added prior to the treatment process may also help to dehornify and deacetylate the biomass. Dehornification refers to rehydration and separation of cellulose and hemicellulose fibers that have adhered together due to drying, thus enhancing the porosity of the biomass, increasing the surface area of exposed cellulose and hemicellulose fibers, and enhancing the rate of mass transfer of the oxidizing agent and oxidized products.

Typically, the amount of base needed for controlling the pH of the treatment mixture is in the range of from about 1 to about 10 wt. %, or from about 1 to about 9 wt. %, or from about 2 to about 9 wt. %, or from about 2 to about 8 wt. %, or from about 2 to about 7 wt. %, or from about 3 to about 7 wt. %, or from about 3 to about 6 wt. %, or from about 4 to about 6 wt. %, based on the dry weight of the biomass.

By controlling the pH in the treatment mixture during the treatment process, the integrity of a significant proportion of the polysaccharides (cellulose and hemicellulose) is preserved in the biomass. The pH adjustment also helps to solubilize lignin and enhance its breakdown by the oxidizing agent. The addition of base to control the pH of the treatment mixture neutralizes acids produced in the treatment process to reduce acid catalyzed hydrolysis of polysaccharides. Specifically, by maintaining the pH of the treatment mixture above pH 4.5, the acid catalyzed hydrolysis of cellulose and hemicellulose is significantly reduced. This leads to preservation of cellulose and hemicellulose in the biomass during the treatment process.

In addition, by limiting most of the oxidation in the treatment process to oxidation of lignin, less carboxylic acids and other small organic molecules that result from oxidization of monosaccharides are produced than would be the case in some prior art processes that do not control pH. Thus, the present invention can be used to increase the potential yield of desirable products of downstream enzymatic or fermentation treatment.

Controlling pH also reduces or prevents secondary repolymerization of the intermediates resulting from oxidization/hydrolysis of lignin, cellulose and hemicellulose during the treatment process, which would otherwise lead to formation of larger, more bio-recalcitrant polymers that are more inert than the original lignocellulosic materials. The present invention also results in the formation of less of these bio-recalcitrant polymers.

By controlling pH to be in the range of pH about 4.5 to about 7.5, the oxidizing agent preferentially targets lignin. A further benefit of preferentially oxidizing lignin is that it reduces the concentration of inhibitors of downstream treatment by enzyme or microorganism. These inhibitors may include, for example, furans including 2-furoic acid, hydroxymethylfurfural, and furfural. In the present process, these inhibitors are solubilized to render them susceptible to fast oxidation by the oxidizing agent to produce acetic acid, formic acid, an eventually carbon dioxide and heat. This chain oxidation of the inhibitors is a beneficial feature of the present invention, since it also progressively consumes oxygen thereby reducing the statistical probability of undesirable oxidation of cellulose and hemicellulose. Thus, this aspect of the process of the present invention self-extinguishes at least some of the potential for oxidation of cellulose and hemicellulose in the biomass by consuming the oxygen.

Figure 2A:
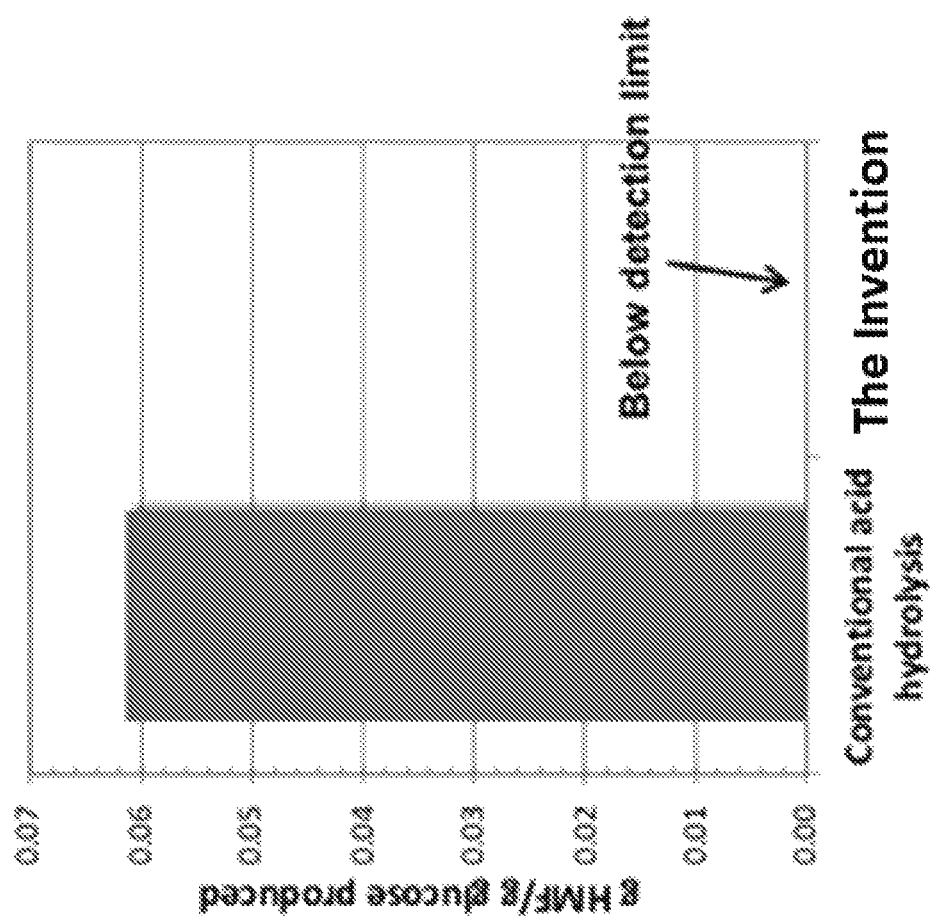
FIGS. 2A-2B are plots showing lower production of the inhibitors furfural and hydroxymethylfurfural (HMF), respectively, by the present process as compared with conventional acid hydrolysis of biomass.
Figure 2B:
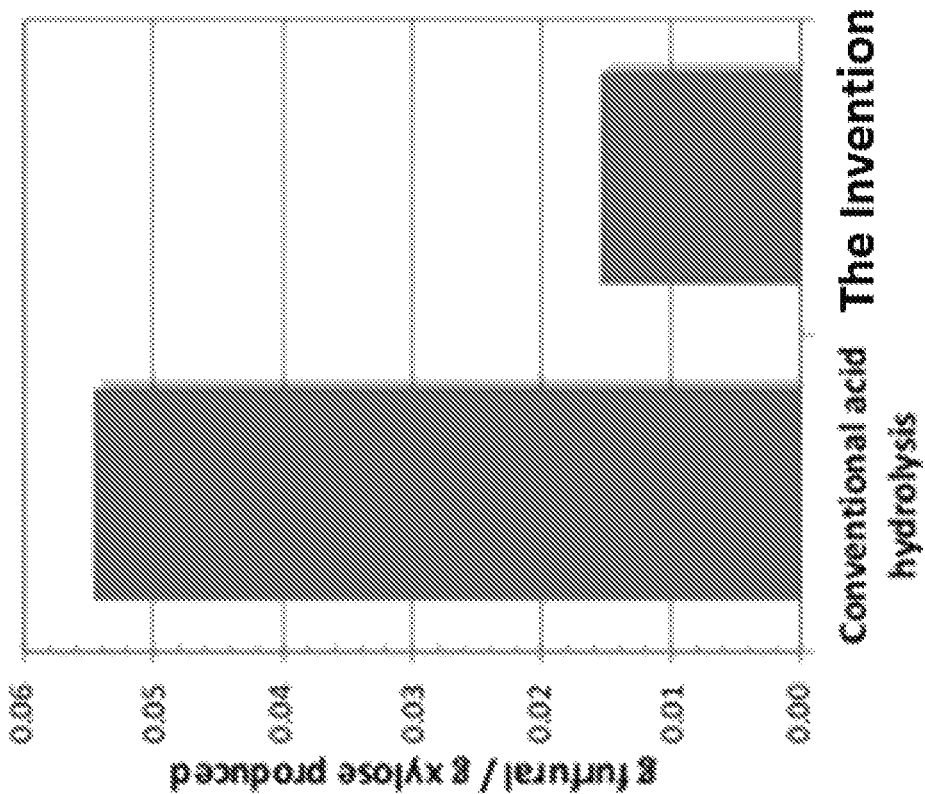

As shown in FIGS. 2A-2B, the present invention very significantly reduces the formation of inhibitors in comparison with conventional acid hydrolysis carried out at a low pH close to 1 using 0.34% $H_2SO_4$. Specifically, the present invention produces significantly less furfural (FIG. 2A) and hydroxymethylfurfural (HMF, FIG. 2B).

Thus, the present invention preferentially oxidizes lignin in the biomass to expose the cellulose and hemicellulose in the biomass for downstream treatment, and also preserves the cellulose and hemicellulose in the biomass. Without pH control, the cellulose and hemicellulose will break down by autocatalytic hydrolysis to produce monosaccharides, which are subsequently subject to oxidation, decomposition, and repolymerization, leading to loss of potential sugars, and lower yields of desirable products from downstream treatments.

During the treatment process, lignin is oxidized to small organic acids and a small amount of carbon dioxide. The lignin is also transformed from hydrophobic to hydrophilic. The partial oxidation of lignin generates heat that reduces the energy cost for heating the biomass during treatment. Further, because lignin is a thermoplastic and expands out of the pores of the biomass with heating, the porosity of the biomass is increased during the treatment process, allowing oxygen to access lignin in the interior of the biomass.

The treatment process significantly increases the accessibility of the cellulose and hemicellulose for downstream enzymatic treatments and/or fermentation processes. This will have a positive influence on downstream reaction kinetics and the degree of conversion of cellulose and hemicellulose to monomeric sugars. The overall yields in the downstream treatments are thus increased. In some embodiments, the yields achieved in the downstream treatments is close to the theoretical yield calculated based on the content of cellulose and hemicellulose in the biomass. Examples of biomass are shown in Table 1.

TABLE 1

Content of Biomass
Moisture Adjusted Additional Feedstock Properties

|  | Wheat straw | Barley Straw | Barley Hay | Corncob | Stover |
|---|---|---|---|---|---|
| Moisture | 10.00 | 10.00 | 10.00 | 10.00 | 10.00 |
| Cellulose | 35.98 | 38.84 | 29.43 | 33.37 | 36.74 |
| Hemicellulose | 19.53 | 18.94 | 10.91 | 27.83 | 20.21 |
| Other Polysaccharides | — | — | — | 3.52 | 4.01 |
| Lignin | 24.46 | 21.04 | 21.45 | 17.04 | 16.50 |
| Ash | 3.51 | 5.07 | 6.86 | 2.92 | 6.79 |
| Others | 6.52 | 6.11 | 21.35 | 5.31 | 5.74 |
| Extractives | — | — | — | — | — |
|  | 100.00 | 100.00 | 100.00 | 100.00 | 100.00 |

The oxidizing agent may be selected from air, oxygen enriched air, oxygen, ozone, sulfuric acid, permanganates, carbon dioxide, nitrous oxide, nitric acid, chromates, perchlorates, persulfates, superoxides, chlorates, peroxides, hypochlorites, Fenton's reagent and nitrates in which the cations may include metal cations, hydrogen ions and/or ammonium ions.

Oxidizing agents may be ranked by their strength. See Holleman et al. "*Inorganic Chemistry*," Academic Press, 2001, page 208. A skilled person will appreciate that, to prevent over-oxidation of the biomass, the conditions in the treatment step may be adjusted to account for the strength of the oxidizing agent. For example, when a strong oxidizing agent is used, one or more of temperature, pressure, and duration of the treatment step may be reduced to prevent over-oxidation and/or ensure that the desired degree of conversion is not exceeded. On the other hand, when a weak oxidizing agent is used, one or more of temperature, pressure, and duration of the treatment step may be increased to ensure that the desired degree of oxidation and/or conversion is achieved. When the oxidizing agent is gaseous, the pressure in the reaction vessel for the treatment step is important for ensuring the desired degree of oxidation and/or conversion. A skilled person can adjust the pressure based on common general knowledge to account for use of a gaseous oxidizing agent.

In some embodiments, oxygen is used as the oxidizing agent. In one embodiment, oxygen can be delivered in air. In some other embodiments, depending on the susceptibility of the biomass to oxidation, oxygen-enriched air can be used. Suitable enrichment can provide an oxygen concentration slightly above that of atmospheric air to an oxygen concentration of substantially pure oxygen.

Oxygen added to the treatment process may be expressed as a weight ratio of the amount of elemental oxygen to the amount of elemental carbon in the biomass (O/C on weight basis). The range of O/C can be from about 0.2 to about 1.0, or from about 0.3 to about 0.9, or from about 0.3 to about 0.8, or from about 0.4 to about 0.7, or from about 0.4 to about 0.6, or from about 0.5 to about 0.6, depending on other conditions of the treatment.

The other component introduced to the treatment process is steam. The steam may be introduced into the biomass or generated in situ from the water in the wet biomass or in the treatment mixture. For example, the biomass may have some moisture, or may be wetted with water before treatment. Once the temperature of the biomass is raised to above 100° C., the moisture or water in the wet biomass or in the treatment mixture will be converted into steam. The amount of steam in the treatment mixture may range from about 0.1 to about 5.0 wt. %, or from about 0.5 to about 4.0 wt. %, or from about 1.0 to about 3.0 wt. %, based on the dry weight of the biomass. Steam may be used for one or both of controlling the pressure of the treatment step and as a heat input to the process.

The temperature of the treatment step is in the range of from about 130° C. to about 220° C., or from about 130° C. to about 210° C., or from about 140° C. to about 210° C., or from about 140° C. to about 200° C., or from about 150° C. to about 200° C., or from about 150° C. to about 190° C., or from about 150° C. to about 180° C., or from about 160° C. to about 180° C., or from about 160° C. to about 170° C.

The treatment mixture may be under an autogenous pressure or under a mild pressure during treatment. For example, the treatment mixture may be under an atmospheric pressure of 201.3 KPa. Alternatively, the pressure may be up to 1114.9 KPa. For example, the pressure may be in the range of from about 201.3 KPa to 2068 KPa, or from about 239.2 KPa to about 1724 KPa, or from about 239.2 KPa to about 1379, or from about 308.2 KPa to about 928.7 KPa, or from about 308.2 KPa to about 790.8 KPa, or from about 308.2 KPa to about 721.9 KPa, or from about 308.2 KPa to about 652.9 KPa, or from about 308.2 KPa to about 584.0 KPa, or from about 308.2 KPa to about 515.0 KPa, or from about 308.2 KPa to about 446.1 KPa, or from about 308.2 KPa to about 377.1 KPa.

The treatment step may be carried out for a period of from about 5 seconds to about 10 hours, or from about 10 seconds to about 9 hours, or from about 20 seconds to about 8 hours, or from about 30 seconds to about 8 hours, or from about 45 seconds to about 8 hours, or from about 1 minute to about 7 hours, or from about 2 minutes to about 7 hours, or from about 5 minutes to about 7 hours, or from about 10 minutes to about 6 hours, or from 15 about minutes to about 6 hours, or from about 20 minutes to about 6 hours, or from about 30 minutes to about 5 hours. In some embodiments, the period for the treatment step may be in the range of from about 5 seconds to about 1 hour, or from about 10 seconds to about 55 minutes, or from about 20 seconds to about 55 minutes, or from about 30 seconds to about 55 minutes, or from about 45 seconds to about 50 minutes, or from about 1 minute to about 50 minutes, or from 2 about minutes to about 50 minutes, or from about 5 minutes to about 50 minutes, or from about 10 minutes to about 40 minutes, or from about 15 minutes to about 40 minutes, or from about 15 minutes to about 30 minutes. In some other embodiments, the period for the treating step may be in the range of from about 1 hour to about 10 hours, or from about 1 hour to about 9 hours, or from about 1 hour to about 8 hours, or from about 1 hour to about 7 hours, or from about 1 hour to about 6 hours, or from about 1 hour to about 5 hours, or from about 1 hour to about 4 hours, or from about 1.5 hours to about 4 hours, or from about 1.5 hours to about 3 hours, or from about 1.5 hours to about 2.5 hours.

It is understood that the temperature, pressure and length of the treating step are all related. For example, when the temperature is high, the length of the treating step may be reduced to prevent over-oxidation of the biomass, or when the pressure is high, the length of the treating step may also be reduced to prevent over-oxidation of the biomass. A severity factor may be used in the practice of the present invention to control the treatment process and prevent over-oxidation of the biomass.

The severity factor (SF) is defined as:

$$SF = \text{Log}\left(t * e^{\frac{T-100}{14.75}}\right)$$

where t is the duration of the treating step in minutes and T is temperature during the treating step in Celsius. It is generally considered that a higher SF value is associated with a larger proportion unwanted by-products that will reduce the yield of desirable products in downstream treatment processes.

In some embodiments, the treating step has a severity factor in the range of from about 2.5 to about 4.5, or from about 2.7 to about 4.3, or from about 2.9 to about 4.1, or from about 3.0 to about 4.0, or from about 3.2 to about 4.0, or from about 3.2 to about 3.8, or from about 3.3 to about 3.7, or from about 3.4 to about 3.6.

Mathematically, the same severity factor may be achieved by using a higher temperature in combination with a shorter treatment period or by using a longer treatment period in combination with a lower temperature. In one embodiment, a higher temperature coupled with a short treatment period may be preferred for reducing the severity factor and thereby reducing secondary polymerization reactions to favor oxidization of lignin.

In some embodiments, the temperature, pressure and/or treatment time may also depend on molecular and elemental characteristics of the biomass. Examples of the characteristics of the biomass which may be taken into consideration are the degree of aromaticity, the hydrogen to carbon ratio of the biomass, the oxygen to carbon ratio of the biomass, the nitrogen to carbon ratio of the biomass, the sulfur to carbon ratio of the biomass, the mineral or ash content of the biomass, as well as other factors known to skilled persons. Thus, in some embodiments, employment of a blend of biomasses having different characteristics may enhance the efficiency of the method by adjusting one or more of these characteristics. For example, blending a highly aromatic biomass with a more acyclic biomass, such as agricultural waste may result in a treatment product that is more biodegradable and will support greater microbial population densities, as well as an increase the rate and depth of conversion of the biomass. Suitable techniques for blending biomass feedstocks are described in US 2012/0160658 A1.

In some embodiments, at least one catalyst may be added to the treatment mixture. The catalyst may catalyze the oxidation reaction by, for example, causing or enhancing formation of peroxides and superoxides, which may enhance the rate of oxygen insertion into the lignin in the biomass.

The catalyst may be selected from water insoluble metals, transition metals, and precious metals, or their salts or oxides. Examples of these metals include nickel, cobalt, platinum, palladium, rhenium, iron, copper, vanadium, zirconium and ruthenium. The catalyst may be unsupported or may be supported on inert or active matrix material such as clay, alumina, silica, silica alumina, zeolites, activated carbon, diatomaceous earth, titania, zirconia, molybdena, ceramics, and the like. Such catalysts can enhance rates of oxygen transfer, insertion and reforming of lignin in the biomass as well as being able to enhance the degree of relative oxidation. Examples of the catalysts include metal oxides, mixed metal oxides, hydroxides, and carbonates, of ceria, lanthanum, mixed rare earths, brucite, hydrotalcite, iron, clays, copper, tin, and vanadium.

In some embodiments, the catalyst is a hydrogenation catalyst including a zirconium/platinum catalyst and zirconium/palladium catalyst. Other catalyst includes noble metals such as Rh, Pd, Pt, Cu, Ru, Pt—Cu, Ni—Cu, $CoMoS_2$, $NiMoS_2$, $MoO_3$, $CrO_3$, $WO_3$, $ZrO_2$, Ni, Ag, Ge, Re, Os, and transition metals such as Li, Na, K, Mg, Ir, Ni, Cu.

In some embodiments, an inert solid may be added to the treatment mixture. The inert solids may include particulate materials such as silica, sand, alumina, silicon, ceramic, zeolite, such as ZSM-5, $CeO_2$, $ZrO_2$, $Al_2O_3$, C, $TiO_2$, $SiO_2$, and oxides or carbonates of Na, K and Mg. The inert solids are preferably present at a particle size in the range of about 50 µM to about 500 µm, more preferably about 200 µm to about 300 µm.

In some embodiments, the catalyst includes a metal ion, especially iron, and a complexing agent may be added to increase solubility of the metal ion in the treatment mixture. In preferred embodiments, all compounds suitable for complexing iron ions are suitable for use in the invention. Types of suitable complexing agents include various oligodentate compounds, crown ethers, exchange resins, etc. Examples of preferred complexing agents include desferrioxamine and desferrioxamine analogs, bacterial or synthetic siderophores, humates (including in situ electrochemically generated humates), EDTA (ethylene diamine tetraacetic acid), EDMA (ethylenediiminobis (2-hydroxy-4-methyl-phenyl) acetic acid), and DTPA (diethylenetriamine-penta acetic acid). Depending on the particular reaction conditions, temperature, pressure and other parameters, the complexing agents may be present at a concentration of between about 0.1 M to about 1.0 M, and more preferably between about 1.0 M to about 2.0 M (and higher). Most preferably, one or more complexing agents are combined to be used in the treatment mixture.

In some embodiments, a pyrophosphate is added to the treatment mixture. Salt and esters containing two phosphate groups are called diphosphates. The anion, the salts, and the esters of pyrophosphoric acid are diphosphates, which are known as pyrophosphates that are chelators. The term "pyrophosphate" also refers to esters formed by the condensation of a phosphorylated biological compound with inorganic phosphate as for dimethylallyl pyrophosphate.

Non-limiting examples of pyrophosphates include sodium pyrophosphate ($NaP_2O_7$), calcium pyrophosphate ($Ca_2P_2O_7$), potassium pyrophosphate ($K_4P_2O_7$), ferrous pyrophosphate, ferric pyrophosphate, pyrophosphoric acid, or derivatives thereof. Derivatives include, for example, hexametaphosphate, sodium hexametaphosphate ($NaPO_3)_6$, sodium tripolyphosphate, and dibasic (e.g., disodium pyrophosphate; dicalcium pyrophosphate, dipotassium pyrophosphate, etc.) and tetrabasic (e.g., tetrasodium pyrophosphate-$Na_4P_2O_7$); tetracalcium pyrophosphate; tetrapotassium pyrophosphate, etc.) salts of cations, mainly sodium, calcium, potassium and iron.

The amount of the pyrophosphate is in the range of from about 0.5 wt. % to about 5 wt. %, or from about 0.5 wt. % to about 4.5 wt. %, or from about 0.75 wt. % to about 4.5 wt. %, or from about 1.0 wt. % to about 4.5 wt. %, or from about 1.0 wt. % to about 4 wt. %, or from about 1.5 wt. % to about 4 wt. %, or from about 1.5 wt. % to about 3.5 wt. %, or from about 2.0 wt. % to about 3.5 wt. %, or from about 2.0 wt. % to about 3.0 wt. %, based on the dry weight of the biomass.

In some embodiments, a deep eutectic solvent (DES) is added to the treatment mixture. The examples of DES include a (2-R-ethyl)-trimethylammonium salt, or a mixture of said salts, and a Lewis acid selected from boric acid, meta-boric acid, boronic acid, borinic acid, alkyl borates, hydrated borate salts, puryvic acid and any combinations thereof. Preferably the Lewis acid is boric acid or pyruvic acid, particularly preferably boric acid. Boric acid refers here to H3BO3, also called as hydrogen borate, boracic acid, ortho-boric acid and acidum boricum.

In the (2-R-ethyl)-trimethylammonium salt, the group R is selected from OH, halogens, ester groups, ether groups and carbamoyl group. The halogens are selected from F, CI, I and Br. The ester groups are suitably selected form formyl, acetyl, isopropyl and butyryl groups. Preferably the R is OH, CI, acetyl or formyl group. The counter anion in the salt can be an inorganic or organic counter anion. The inorganic salt is suitably a halogenide, sulphate or phosphate, preferably chloride salt. The organic salt is suitably acetate, lactate, butyrate or formiate.

Preferably the (2-R-ethyl)-trimethylammonium salt is selected from choline chloride, acetylcholine chloride, and chlorocholine chloride, particularly preferably choline chloride. Choline chloride is a widely available material and it is used for example as low cost animal feed.

In some embodiments, a layered metal hydroxy salt is added to the treatment mixture. Examples of metal hydroxy salts include hydroxy salts of a divalent metal having a formula: $[(Me^{2+}, M^{2+})_2(OH)_3]^+(X^{n-})_{1/n}]$, wherein $Me^{2+}$ and $M^{2+}$ may be the same or different divalent metal ions and $X^{n-}$ is an anion other than OFF. Another formula for the hydroxy salts may be $[(Me^{2+}, M^{2+})_5(OH)_8]^{2+}(X^{n-})_2/n]$, wherein $Me^{2+}$ and $M^{2+}$ may be the same or different divalent metal ions and $X^{n-}$ is an anion other than OFF.

If the metal hydroxy salts contain two different metals, the ratio of the relative amounts of the two metals may be close to 1. Alternatively, this ratio may be much higher, meaning that one of the metals predominates over the other. Examples of suitable layered hydroxy salts with one type of metal are Zn-hydroxy salt (e.g. $Zn_5(OH)_8(X)_2$, $Zn_4(OH)_6X$, $Zn_5(OH)_6(X)_2 \cdot H_2O$, $Zn_3(OH)_4(X)_2$), Co-hydroxy salt (e.g. $Co_2(OH)_3X$, Ni-hydroxy salt (e.g. $Ni_2(OH)_3X$), Mg-LHS (e.g. $Mg_2(OH)_3X$), Fe-hydroxy salt, Mn-hydroxy salt, and La-hydroxy salt ($La(OH)_2NO_3$). Examples of suitable layered hydroxy salts including two or more different types of metals are Zn—Cu hydroxy salt, Zn—Ni hydroxy salt, Zn—Co hydroxy salt, Fe—Co hydroxy salt, Zn—Mn hydroxy salt, Zn—Fe hydroxy salt, Ni—Cu hydroxy salt, Cu—Co hydroxy salt, Cu—Mg hydroxy salt, Cu—Mn hydroxy salt, Fe—Co hydroxy salt, Ni—Co hydroxy salt, Zn—Fe—Co hydroxy salt, Mg—Fe—Co hydroxy salt, and Ni—Cu—Co hydroxy salt. Especially preferred layered hydroxy salts are Zn—Mn hydroxy salt and Zn—Fe hydroxy salt.

Examples of suitable interlayer anions $X^{n-}$ are $NO_3^-$, $OH^-$, $Cl^-$, $Br^-$, $I^-$, $SO_4^{2-}$, $SiO_3^{2-}$, $CrO_4^{2-}$, $BO_3^{2-}$, $MnO_4^-$, $HGaO_3^{2-}$, $HVO_4^{2-}$, $ClO_4^-$, $BO_3^{2-}$, pillaring anions such as $V_{10}O_{28}^{6-}$ and $Mo_7O_{24}^{6-}$, monocarboxylates such as acetate, dicarboxylates such as oxalate, and alkyl sulfonates such as lauryl sulfonate.

In some embodiments, at least one hydrated inorganic salt of formula (I): $MX_n \cdot n'H_2O$, where M is a metal that is selected from groups 1 to 13 of the periodic table, X is an anion, n is an integer between 1 and 6, and with n' being between about 0.5 and about 12. In one embodiment, a mixture of hydrated inorganic salts can be used for baking the dried solid fraction. The anion X can be a monovalent, divalent, or trivalent anion. In a preferred way, the anion X is a halide anion that is selected from among $Cl^-$, $F^-$, $Br^-$, and $I^-$, a perchlorate anion ($ClO_4^-$), a thiocyanate anion ($SCN^-$), a nitrate anion ($NO_3^-$), a para-methylbenzene sulfonate anion ($CH_3-C_6H_4-SO_3^-$), an acetate anion ($CH_3COO^-$), a sulfate anion ($SO_4^{2-}$), an oxalate anion ($C_2O_4^{2-}$), or a phosphate anion ($PO_4^{3-}$). In an even more preferred way, the anion X is a chloride.

In a preferred embodiment, the metal M in formula (I) is selected from among lithium, iron, zinc, or aluminum. In a particularly preferred embodiment, the hydrated inorganic salt is selected from among: $LiCl \cdot H_2O$, $LiCl \cdot 2H_2O$, $ZnCl_2 \cdot 2.5H_2O$, $ZnCl_2 \cdot 4H_2O$ and $FeCl_3 \cdot 6H_2O$.

In some embodiments, an organic solvent solution may be added to the treatment mixture. The organic solvent solution may be an organic solvent mixture in water that includes any organic liquid that dissolves a solid, liquid, or gaseous solute, resulting in a solution. The most suitable solvent solutions for this invention are organic solvents such as ethanol, methanol, n-propanol, isopropanol, n-butanol, 2-butanol, isobutanol, t-butanol, pentanol, hexanol and diols with the same number of carbons. They can also include aprotic solvents. The solvent solutions can include additional components in mixture with the solution, e.g., one or more nucleophiles.

The treatment may use either a horizontal reactor or a vertical reactor. The reactor is not limited to any particular reactor design, but may be any sealable reactor suitable for operation at the temperature and pressure required for the present process. In some embodiments, the mixture is fed to a reactor, which has been pre-heated to the desired temperature. Then, air or oxygen enriched air is slowly added to the reactor until the desired pressure is reached. The temperature and pressure in the reactor may be monitored during the filling of air or oxygen enriched air, as well as any heating of the mixture. Some suitable reactor designs are high solid reactors employing screw or auger transport such as these described in Kelkar et al. ("Pyrolysis of spent coffee grounds using a screw-conveyor reactor," *Fuel Processing Technology*, vol. 137, pp. 170-178, (2015) described in Blume ("Bitumen blowing unit converts residues to asphalt," *Hydrocarbon Processing*, March 2014).

The treatment mixture in the reactor has at least two phases, a liquid phase of e.g. water, solubilizing agent and/or oxidizing agent, and a solid phase biomass and optional catalyst or inert materials. In many embodiments, there are three phases in the reactor: gas (oxygen, air and/or steam), liquid (water and/or solubilizing agent) and solid (biomass). To ensure efficient heat and mass transfer among these phases, the mixture may be subjected to mechanical agitation. The reactor may include structural features to facilitate interactions among the phases. The mixture may have high solid content and high cohesion, the screw/auger based transport may be used to stir the mixture and move the mixture along the reactor as commonly used in biomass pyrolysis or gasification. For example, an unstirred reactor with gas dispersion features, a reactor with mechanical agitation devices as well as a reactor with gas entrainment devices or combinations thereof. Exemplary reactors include a co-current flow tubular reactor with gas dispersion, a counter-current flow tubular reactor with gas dispersion, and a flowing tubular reactor with static mixers.

In some embodiments, the biomass may be preprocessed (e.g., comminuted) to increase its permeability or available surface area. Any method known to a skilled person that is suitable for reducing the particle size of biomass may be used. For example, physical (e.g., grinding, milling, fracture and the like) and chemical approaches (e.g., treating with surfactants, acids, bases, oxidants, such as but not limited to acetic acid, sodium hydroxide, percarbonate, peroxide and the like) can be applied to reduce the size of the biomass particles.

Mechanical means may be used to commute the biomass by a combination of chipping, grinding, and/or milling.

Biomass may also be comminuted after treatment. For instance, steam explosion processes use explosive decompression of steam and other entrained gases with the biomass particles/pieces to significantly reduce the particle size of coarsely chipped biomass and delaminate the cellulose bundles, whereas other mechanical processes commonly employ a secondary grinding or milling step, i.e., a disc refiner, to further reduce the particle size and deliberate the treated biomass chipped biomass. Chipped biomass has a characteristic dimension of 1-3 cm, compared to milled or ground material, which has a characteristic dimension of 0.2-2.0 mm. J. D. McMillan, "*Processes for Pretreating Lignocellulosic Biomass: A Review*," National Renewable Energy Laboratory, NREL/TP-421-4978 (November 1992). Some suitable preprocessing methods are described in US 2010/0139913, WO 2010/1071533 and US 2010/0262987.

In some embodiments, the preprocessing may include additional steps of prewashing and/or preheating the biomass to remove undesirable contaminants from the biomass. In one example, prewashing may be carried out using an inclined wash table and several mass equivalents of hot demineralized water. The wash water, at a temperature of about 50 to 60° C. at the point of contact with the biomass, is distributed onto the biomass over a period of about 5 to 10 minutes.

This prewashing step offers multiple benefits for the treatment process. First, washing removes a significant portion, e.g. greater than 80 wt. % of the non-structural ash (dirt) carried within or on the biomass. Sand, rock, and dirt intermixed with the biomass accelerates the erosion and plugging of pipes, valves, and rotating equipment used in the treatment and downstream biological conversion steps. Cleaning the biomass ahead of treatment significantly reduces maintenance and operational costs in commercial operations, while increasing yields and overall facility efficiency.

Additionally, warm wash water successfully removes over 80% of the chloride resident within or on biomass such as harvested corn stover. It is highly beneficial to reduce the chloride level of biomass to concentrations under 200 ppmw. In doing so, cheaper stainless-steel alloys, like duplex stainless steel, can be used in the treatment reactor and other heated sections of the physical plant. At these lower levels of chloride, corrosion rates at the temperatures experienced in treatment are reduced to a level that does not require the use of more exotic expensive alloys.

Furthermore, the prewashing step encourages some amount of re-wetting, swelling, and pore and fiber bundle opening of field-dried or oven-dried biomass, like corn stover. Hydration increases accessibility to the bulk of the biomass and doing so enables greater rates of mass transfer of reactants, oxidizing agent, and solubilized intermediates in and out of the solid biomass during treatment. This may also shorten residence time in the reactor.

Moreover, the prewashing step permits the removal and recovery of water-soluble monomeric and oligomeric sugars and other soluble components present in the biomass, known collectively as extractives. For example, depending on the age and condition of corn stover, extractives can account for more than 20 wt. % of the dry weight and more than 44 wt. % of the total extractable mass can be carbohydrates. The extractives may be used for downstream applications such as growth of fungi or fermentation.

In some embodiments, the treatment product is used for downstream enzymatic treatment. A single enzyme or a cocktail of enzymes may be used. Useful enzymes include xylanases, cellulases, hemicellulases, xylosidase, esterase, arabinofuranosidase, galactanase, oxidases, peroxidases, mannases, laccases, oxidoreductases, pectinases, lipases and any combinations thereof.

The cellulase is preferably selected from cellobiohydrolases (EC 3.2.1.–), endo-1,4-β-glucanase (EC 3.2.1.4), β-glucosidase (EC 3.2.1.4), cellobiose hydrolase (EC 3.2.1.21), glycoside hydrolase 61 (GH61 and CBM33), Expansin, Swollenin, Loosinin and CIP Proteins (EC 3.1.1.–; CE15). The hemicellulase includes any enzyme or blend of enzymes capable of degrading or supporting the degradation of hemicellulose.

Another enzyme may be used is Arabinan endo-1,5-alpha-L-arabinosidase, referring to Arabinan endo-1,5-alpha-L-arabinosidase EC 3.2.1.99, which is expressed by some bacteria or fungi. Arabinan endo-1,5-alpha-L-arabinosidase is preferably derived from fungi such as *Aspergillus terreus, Bacillus subtilis, Aspergillus oryzae, Fomes fomentarius, Penicillium chrysogenum, Aspergillus aculeatus, Cylindro carponcongoense, Nectria haematococca, Myceliophthora thermophile, Chaetomium globulosum, Trametes versicolor* or *Aspergillus nidulans*. The Arabinan endo-1,5-alpha-L-arabinosidase may be produced by expression in an endogenous organism or may be produced by expression in a heterologous organism.

Suitable hemicellulases include β-glucanases (EC 3.2.1.–), endo-xylanase (EC 3.2.1.8), β-xylosidase (EC 3.2.1.37), acetylxylan esterase (EC 3.1.1.72), acetylgalactan esterase (3.1.1.6), acetyl mannan esterase, feruloyl esterase (EC 3.1.1.73), glucuronoyl esterase (EC 3.1.1.–), a-L-arabinofuranosidase (EC 3.2.1.55), a-arabinopyranosidase (3.2.1.–), a-galactosidase (EC 3.2.1.22), β-galactosidase (EC 3.2.1.23), a-glucuronidase (EC 3.2.1.139), β-mannase (EC 3.2.1.78), β-mannosidase (EC 3.2.1.25), mannan 1,4-mannobiosidase (EC 3.2.1.100), arabinogalactan endo-beta-1,4-galactanase (EC 3.2.1.89), endo-beta-1,3-galactanase (EC 3.2.1.90), galactan endo-beta-1,3-galactanase (EC 3.2.1.181, glucuronoarabinoxylan endo-1,4-beta-xylanase (EC 3.2.1.136), alpha-L-fucosidase (EC 3.2.1.51), coniferin beta-glucosidase (EC 3.2.1.126), xyloglucan hydrolases (EC 3.2.1.150, 151, 155), xylan a-1,2-glucuronosidase (EC 3.2.1.131), endo-xylogalacturonan hydrolases (EC 3.2.1.–; GH28), a-amylase (EC 3.2.1.1), glucan 1,4-a-glucosidase (EC 3.2.1.3), galactan 1,3-galactosidase (GH43), -1,4,-endogalactanases (EC 3.5.1.89; GH53), a-rhamnosidase (EC 3.2.1.40), β-rhamnosidase (EC 3.2.1.43), lignin peroxidase (EC 1.11.1.14), Mn peroxidase (EC 1.11.1.13), aryl-alcohol oxidase (EC 1.1.3.7), glyoxal oxidase (EC 1.1.3.), carbohydrate oxidases (EC 1.1.3.4, 9, 10), and cellobiose dehydrogenase (EC 1.1.99.18).

A pectinase refers to any enzyme capable of degrading or supporting the degradation of pectin. Suitable pectinases include polygalacturonases (EC 3.2.1.15, 67, 82; GH28), pectin-pectatelyases (EC 4.2.2.2, 6, 9, 10), pectin methyl esterase (EC 3.1.1.11), pectin acetyl esterases (EC 3.1.1.–), rhamnogalacturonases (EC 3.2.1.–; GH28), rhamnogalacturonanacetylesterase (EC 3.1.1.86), rhamnogalacturonanendo lyase (EC 4.2.2.23), rhamnogalacturonanlyases (EC 4.2.2.–), rhamnogalacturonangalacturonohydrolases (EC 3.2.1.–), xylogalacturonan hydrolases (EC 3.2.1.–), pectin methylesterase (EC 3.1.1.11), beta-arabinofuranosidase (EC 3.2.1.55), beta-1,4-galactanase (EC 3.2.1.89), beta-1,3-galactanase (EC 3.2.1.90), beta-galactosidase (EC 3.2.1.23), alpha-galactosidase (EC 3.2.1.22), feruloyl acetyl esterases (EC 3.1.1.–), alpha-fucosidase (EC 3.2.1.51), beta-fucosidase (EC 3.2.1.38), beta-apiosidases (EC 3.2.1.–), alpha-rhamnosidase (EC 3.2.1.40), beta-rhamnosidase (EC 3.2.1.43), alpha-arabinopyranosidases (EC 3.2.1.–), beta-glucuronidase (EC 3.2.1.31), alpha-glucuronidase (EC 3.2.1.139), beta-xylosidase (EC 3.2.1.37) and alpha-xylosidases (EC 3.2.1.–).

The enzymes used for the downstream treatment generally have a preferred pH range of from pH 4.5 to pH 7.0, or from pH 5.5 to pH 6.5. Thus, the treatment product may be directed to a downstream enzymatic treatment without pH adjustment.

In some embodiments, the treatment product is used for downstream fermentation by bacteria, yeasts and/or fungi (single cell or multi-cell fungi). Fermentation uses one of the microorganisms described herein to grow in or on the treatment product. As a result of treatment, the microorganisms have enhanced access to the cellulose and hemicellulose in the treatment product (treated biomass). Thus, the efficiency of fermentation is enhanced in comparison with biomass that has not been treated. Further the preservation of cellulose and hemicellulose in the biomass provides more substrate for the microorganisms to grow, in comparison with the prior art treatment processes where a significant portion of the cellulose and hemicellulose may be destroyed.

In some embodiments, at least one wood rot fungus may be used for the fermentation. "Wood rot fungi" refer to fungi that are capable of degrading wood including members of the phylum Basidomycota. The two major classes of wood rot basidiomycetes are white rot fungi, such as members of the *Phanerochaete* genus (e.g. *P. chrysosporium*) and *Coprinopsis* genus (e.g. *C. cinerea*), and brown rot fungi.

White rot fungi produce a broad array of cellulases and hemicellulases as well as peroxidases, manganese peroxidases, copper radical oxidases, cellobiose dehydrogenase, and pyranose-2-oxidase that interact to promote rapid depolymerization of wood (Martinez, D., et al., Genome, transcriptome, and secretome analysis of wood decay fungus *Postia placenta* supports unique mechanisms of lignocellulose conversion, *Proc Natl Acad Sci USA*, 2009. 106(6): p. 1954-9; and Vanden Wymelenberg, A., et al., Comparative transcriptome and secretome analysis of wood decay fungi *Postia placenta* and *Phanerochaete chrysosporium*, *Appl Environ Microbiol*, 2010. 76(11): p. 3599-610). Brown rot fungi produce an array of hemicellulases but are less efficient in cellulases production (Vanden Wymelenberg, A., et al., Comparative transcriptome and secretome analysis of wood decay fungi *Postia placenta* and *Phanerochaete chrysosporium*, *Appl Environ Microbiol*, 2010. 76(11): p. 3599-610). The brown rot fungi appear to rely more heavily on oxidative mechanisms for cellulose depolymerization.

Some exemplary embodiments for fermentation of the treatment product include:

Fermentation into ethanol of $C_6$ sugars by a yeast, for example a yeast that belongs to the genus *Saccharomyces* (*S. cerevisiae, S. carlsbergensis, S. bayanus, S. uvarum*), *Schizosaccharomyces* (*S. pombe*) or else *Kluyveromyces* (*K. fragilis*);

Fermentation into solvents such as acetone, butanol, by a bacterium, such as, for example, that of the genus *Clostridium*; and Fermentation into ethanol of $C_6$ and $C_5$ sugars by a yeast such as, for example, *Pichia Stipitis* or *Candida Sheatae* or *Pachysolen tannophilus*; or by a bacterium such as, for example, *Zymomonas mobilis*; or else by a genetically modified yeast for producing $C_5$ sugars.

Fermentation may be carried out in a microbial digester, where the treatment product undergoes a bioconversion process wherein some, or all, of the cellulose and hemicellulose in the treatment product are digested. In one embodiment, the bioconversion process may produce biogases such as methane, hydrogen, carbon monoxide, other gases and mixtures thereof, which may be used as fuel or can be converted to electricity. In another embodiment, the bioconversion process may produce small molecule sugars, alcohols, small molecule hydrocarbons that are useful in the chemical industry.

The conditions in the microbial digester should be optimized to achieve the greatest biodegradation of the treatment product in the digester, including one or both of the degree and rate of bioconversion. The microbial digester may be an aerobic digester or an anaerobic digester, or a combination of the two. In an aerobic digester, oxygen is supplied, which generally leads to fast breakdown of the treatment product. In an anaerobic digester, no oxygen is supplied and thus breakdown of the treatment product is generally slower. Aerobic and anaerobic digestion typically provide different products. Thus, in some cases a combination aerobic and anaerobic digestion may function complimentarily.

In some embodiments, the microbial digester may be a partial anaerobic digester, which may be configured such that only an initial portion of the microbial digester is exposed to oxygen. At a downstream portion of the microbial digester, the oxygen has been essentially consumed and thus this portion of the microbial digester functions as an anaerobic digester. In this partial anaerobic digester, the carbonaceous materials pass from the aerobic portion to anaerobic portion and thus are subjected to both aerobic and anaerobic digestion. In some embodiments, the microbial digester may be supplied with a less than stoichiometric amount of oxygen. After the initial aerobic digestion, the oxygen is essentially consumed. Then the digester becomes an anaerobic digester.

Microorganisms may be used in the form of a single species or strain of a microorganism, multiple species or strains of microorganism or a microorganism consortium. Different microorganisms may be employed for different purposes. For example, two or more different reactions may be carried out in a single microbial digester by introduction of different microorganisms. Concentrations of microorganisms may also be varied to alter the relative reaction rates thereby influencing the reaction product mixture, particular in situations where reactions compete for the same reactants. A particular microorganism that is involved in a rate-limiting step of the bioconversion process may be supplemented to increase the reaction rate or yield of that rate-limiting step.

In embodiments employing a microorganism consortium, different species of microorganisms may be provided for different purposes. For example, a particular microorganism can be introduced for the purpose of increasing a nutrient, decreasing a concentration of a toxin, and/or inhibiting a competing microorganism for another microorganism in the consortium that participates in the conversion process. One or more species of microorganisms may be introduced to accomplish two or more of these purposes.

The microorganisms may be naturally occurring or may be synthesized from naturally occurring strains. Furthermore, the microorganisms may incorporate genetically modified organisms. These microorganisms may include fungi, bacteria, archaea, and combinations thereof. The microorganisms are typically selected based on metabolic pathways that achieve conversion of cellulose and hemicellulose to specific products of interest.

In some embodiments, at least one nutrient may be introduced to the microbial digester. The nutrients may be substances upon which one or more species of microorganism is dependent or nutrients that can or will be converted to a substance upon which one or more species of microorganism is dependent. Suitable nutrients for the present invention include ammonium, ascorbic acid, biotin, calcium, calcium pantothenate, chlorine, cobalt, copper, folic acid, iron, $K_2HPO_4$, $KNO_3$, magnesium, manganese, molybdenum, $Na_2HPO_4$, $NaNO_3$, $NH_4Cl$, $NH_4NO_3$, nickel, nicotinic acid, p-aminobenzoic acid, biotin, lipoic acid, mercaptoethane-sulfonic acid, nicotinic acid, phosphorus, potassium, pyridoxine HCl, riboflavin, selenium, sodium, thiamine, thioctic acid, tungsten, vitamin B6, vitamin B2, vitamin B1, vitamin B12, vitamin K, yeast extract, zinc and mixtures of one or more of these nutrients.

In some embodiments, at least one enzyme may also be added to the microbial digester. The enzymes can be used, for example, to enhance the conversion of the treatment product. For example, an enzyme may be used to assist a specific conversion reaction, preferably a rate limiting reaction, in the bioconversion process. In some exemplary embodiments, enzymes may be used to further to enhance the yield, rate and/or selectivity of the bioconversion process, or a substance that inhibits growth of at least one species inhibitory to the yield, rate and/or selectivity of the conversion process.

The enzymes that may be introduced into the microbial digester include Acetyl xylan esterase, Alcohol oxidases, Allophanate hydrolase, Alpha amylase, Alpha mannosidase, Alpha-L-arabinofuranosidase, Alpha-L-rhamnosidases, Ammoniamonooxygenase, Amylases, Amylo-alpha-1,6-lucosidase, Arylesterase, Bacterial alpha-L-rhamnosidase, Bacterial pullanases, Beta-galactosidase, Beta-glucosidase, Carboxylases, Carboxylesterase, Carboxymuconolactone decarboxylase, Catalases, Catechol dioxygenase, Cellulases, Chitobiase/beta-hexo-aminidase, CO dehydrogenase, CoA ligase, Dexarboxylases, Dienelactone hydrolase, Dioxygenases, Dismutases, Dopa 4,5-dioxygenase, Esterases, Family 4 glycosylhydrolases, Glucanaeses, Glucodextranases, Glucosidases, Glutathione S-transferase, Glycosyl hydrolases, Hyaluronidases, Hydratases/decarboxylases, Hydrogenases, Hydrolases, Isoamylases, Laccases, Levansucrases/Invertases, Mandelate racemases, Mannosyl oligosaccharide glucosidases, Melibiases, Methanomicrobialesopterin S-methyltransferases, Methenyl tetrahydromethanopterin cyclohydrolases, Methyl-coenzyme M reductase, Methylmuconolactone methyl-isomerase, Monooxygenases, Muconolactone delta-isomerase, Nitrogenases, O-methyltransferases, Oxidases, Oxidoreductases, Oxygenases, Pectinesterases, Periplasmic pectate lyase, Peroxidases, Phenol hydroxylase, Phenol oxidases, Phenolic acid decarboxylase, Phytanoyl-CoA dioxygenase, Polysaccharide deacetylase, Pullanases, Reductases, Tetrahydromethan-opterin S-methyltransferase, *Thermotoga* glucanotransferase and Tryptophan 2,3-dioxygenase.

In some embodiments, the pretreatment product may be suitable for use in agricultural applications as fertilizers, soil enhancers, or base for growing compost or growing medium. There are agriculturally valuable organisms that can grow on or use the cellulose and/or hemicellulose, as well as fluvic and humic acids, in the treatment product. For example, the treatment product may be used in soilless growth of vegetables, fruit plants, or decorative plants. Another example is that the treatment product may be used as fertilizer for grasses (residential lawn). In another example, the treatment product can be used to increase the soil microbiota, and in particular, nitrogen fixing bacteria, which reduces the need for nitrogen fertilizers. Further, the treatment product may be the base in compost to be used in gardening or farming. Finally, the treatment product may be used as a base for growth of fungi.

The fermentation and agricultural applications preferably require a pH in the range of pH about 5.5 to about 7.5. The treatment process that produces product for the fermentation and agricultural applications preferably also has a controlled pH in the range of pH about 5.5 to about 7.5. Thus, the treatment product may be directly used without pH adjustment in these applications.

The amount of base needed in the present process to produce the treatment product suitable for direct use in the downstream treatment processes without pH adjustment has been found to be much less than the amount of base required to adjust the treatment product of prior art processes into the same pH range. This appears to be the result of the failure to control the pH during the prior art treatment processes. It is theorized that this may be because controlling the pH of treatment process results in production of less carboxylic acids and carbonic acid during the treatment step. As a result, less total base is needed to neutralize the acids to provide treatment products having the desired pH. In some cases, the reduction of the base realized by the present process is at least about 40%, or at least about 50%, or at least about 60%, or at least about 70% of the base needed in the prior art process as exemplified by prior art processes carried out at a pH of less than 4.5.

The products from the downstream treatment (enzymatic treatment or fermentation) include oxygenated hydrocarbons include alcohols, aldehydes, carboxylic acids, salts of carboxylic acids, esters, ethers, anhydrides, and like. Oxygenated compounds may be monofunctional, difunctional, trifunctional, or polyfunctional. Included in the definition of oxygenated hydrocarbons are also compounds with more than one functional group, such as polyols, dicarboxylic acids, triacids, polyesters, polyethers, aldehydic acids, and like. Included in the definition of oxygenated hydrocarbons are also compounds in which there is more than one functional group wherein the functional groups are different.

Examples of carboxylic acids include compounds of the formula RCOOH, wherein R is an alkyl group. Particular examples include formic acid, methanoic acid, acetic acid, ethanoic acid, propionic acid, butyric acid, butanoic acid, valeric acid, pentanoic acid, caproic acid, hexanoic acid, enanthic acid, heptanoic acid, caprylic acid, octanoic acid, pelargonic acid, nonanoic acid, capric acid, decanoic acid, undecylic acid, undecanoic acid, lauric acid, dodecanoic acid, tridecylic acid, tridecanoic acid, myristic acid, tetradecanoic acid, pentadecanoic acid, palmitic acid, hexadecanoic acid, margaric acid, heptadecanoic acid, stearic acid, octadecanoic acid, arachidic acid, and icosanoic acid.

Dicarboxylic acids of the present invention are organic compounds that contain two carboxylic acid groups. Such dicarboxylic acids may include additional heteroatoms, such as oxygen, nitrogen, or sulfur. Dicarboxylic acids may be aliphatic or aromatic. Aside from the two COOH groups, dicarboxylic acids may be saturated or unsaturated. The dicarboxylic acids may be represented by the formula HOOCRCOOH, wherein R is a difunctional organic group, such as alkylene, alkenylene, alkynylene, arylene, and any of the preceding modified by one or more heteroatoms.

Dicarboxylic acids include compounds such as alkylene dicarboxylic acids, having the general formula $HOOC(CH_2)_nCOOH$ wherein n is 0 to 12; mono-unsaturated forms thereof; di-unsaturated forms thereof; tri-unsaturated forms thereof, and polyunsaturated forms thereof.

Examples of dicarboxylic acids include oxalic acid, ethanedioic acid, malonic acid, propanedioic acid, succinic acid, butanedioic acid, glutaric acid, pentanedioic acid, adipic acid, hexanedioic acid, pimelic acid, heptanedioic acid, suberic acid, octanedioic acid, azelaic acid, nonanedioic acid, sebacic acid, decanedioic acid, undecanedioic acid, and dodecanedioic acid.

Examples of aromatic dicarboxylic acids include phthalic acid, benzene-1,2-dicarboxylic acid, o-phthalic acid, isophthalic acid, benzene-1,3-dicarboxylic acid, m-phthalic acid, terephthalic acid, benzene-1,4-dicarboxylic acid, and p-phthalic acid.

Examples of monounsaturated acids include maleic acid, (Z)-butenedioic acid, fumaric acid, (E)-butenedioic acid, glutaconic acid, pent-2-enedioic acid, traumatic acid, and dodec-2-enedioic acid.

Example of di-unsaturated acids includes three isomeric forms of muconic acid, and (2E,4E)-hexa-2,4-dienedioic acid.

The conversion of carbons in biomass to liquid products after the downstream treatment may be measured as dissolved organic carbon (DOC). The DOC including volatile fatty acids (VFA), dicarboxylic acids (DCA), volatile organic compounds (VOC), C5 and C6 sugars, carbon dioxide, and so on, can account for from about 10 to about 50% of the carbon in the biomass. Conversion to gaseous products, primarily $CO_2$ is minimized in the present invention (loss of carbon thus reducing yields) and in the ranges 2-10% of the carbon in the biomass.

EXAMPLES

The following examples are illustrative, but not limiting, of the methods of the present disclosure. Other suitable modifications and adaptations of the variety of conditions and parameters normally encountered in the field, and which are obvious to those skilled in the art, are within the scope of the disclosure.

Example 1. Relation Between Base Addition and Treatment Severity Factor

In this example, corn stover (milled to small particles) was oxidized with oxygen in treatments with different bases to assess the impact of different bases on the severity factor. When the base was NaOH, an equation was developed to establish the dependency of severity factor on the amount of base, namely, % NaOH=0.0755*SF-0.2173, which formula was used to calculate the amount of NaOH needed to control the pH of the treatment mixture to be about pH 5 and ensure that the treatment product had a pH of about 5.

Figure 3:
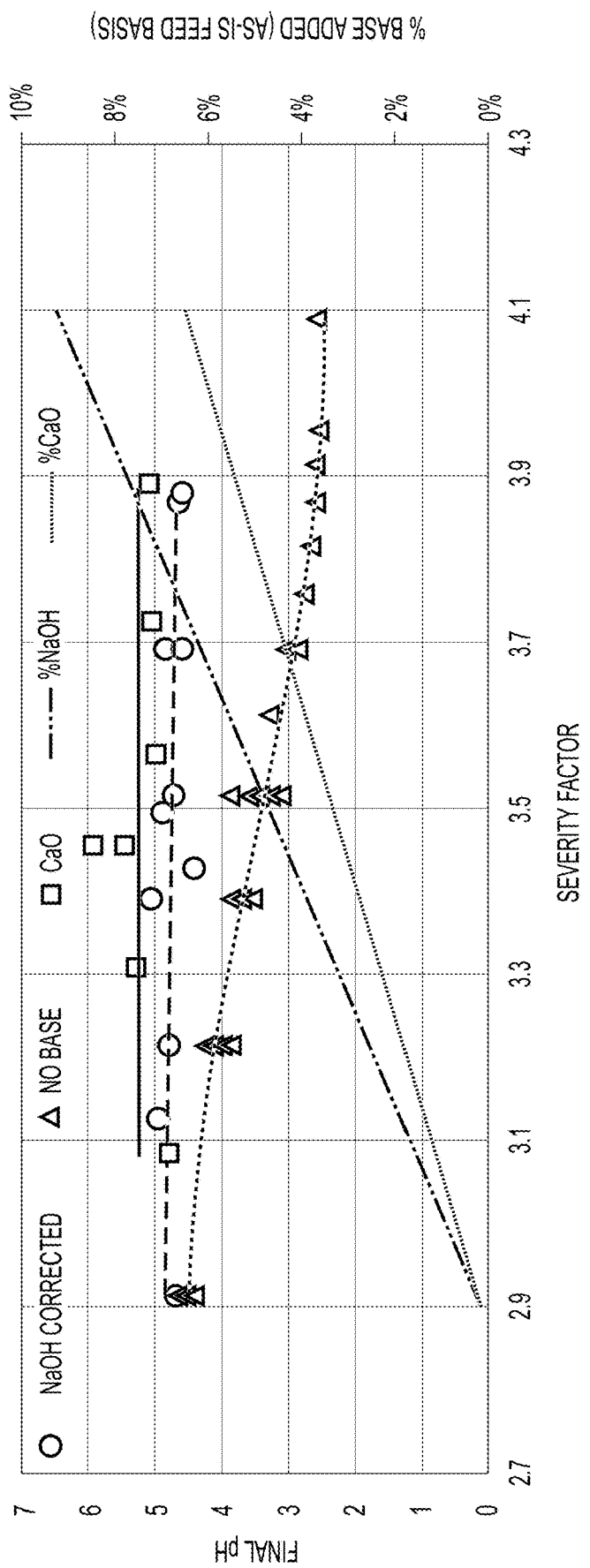
FIG. 3 is plot showing the relationship between severity factor, pH and the amount of base added during the treatment process.

This equation was applicable for a batch process treating corn stover wherein: $3 \leq SF \leq 4$, % O/C≈90%, the initial gas pressure≈596 psi, % Solids≈6. The severity factor ($3 \leq SF \leq 4$) used for corn stover corresponded to 165° C. for a 10 to 120 min treatment period. The equation was also found to be accurate when extrapolated to other bases such as CaO, $NaHCO_3$, $Na_2CO_3$, $NH_4OH$ and urea by adjusting for the molecule weight and functionality of these bases (FIG. 3).

This equation was proven effective for maintaining a constant pH and suitable severity factor for other biomasses such as sugarcane bagasse (SCB). However, the resultant pH may not be exactly 5, indicating that if a particular pH is desired, an adjustment for different biomasses may be needed.

Figure 4:
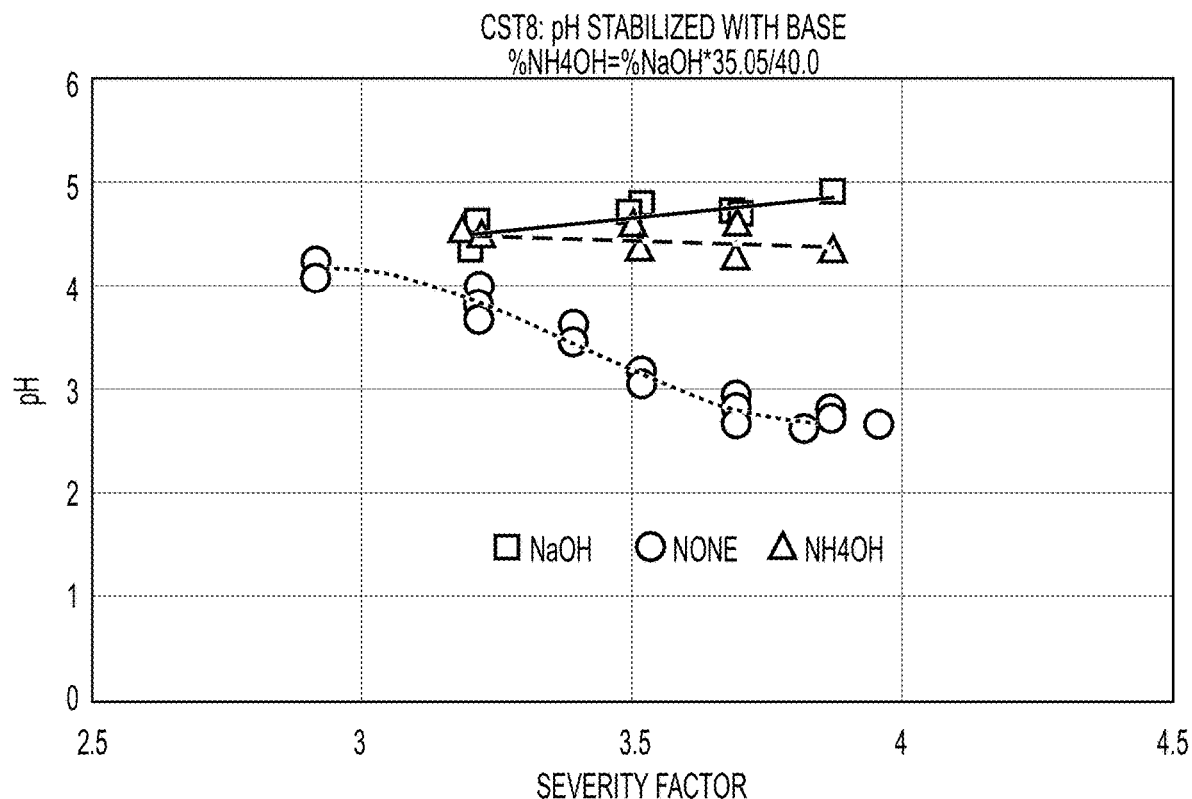
FIG. 4 is plot comparing two bases: NaOH and $NH_4OH$ in maintaining pH during the treatment process at various levels of severity factor.
Figure 5:
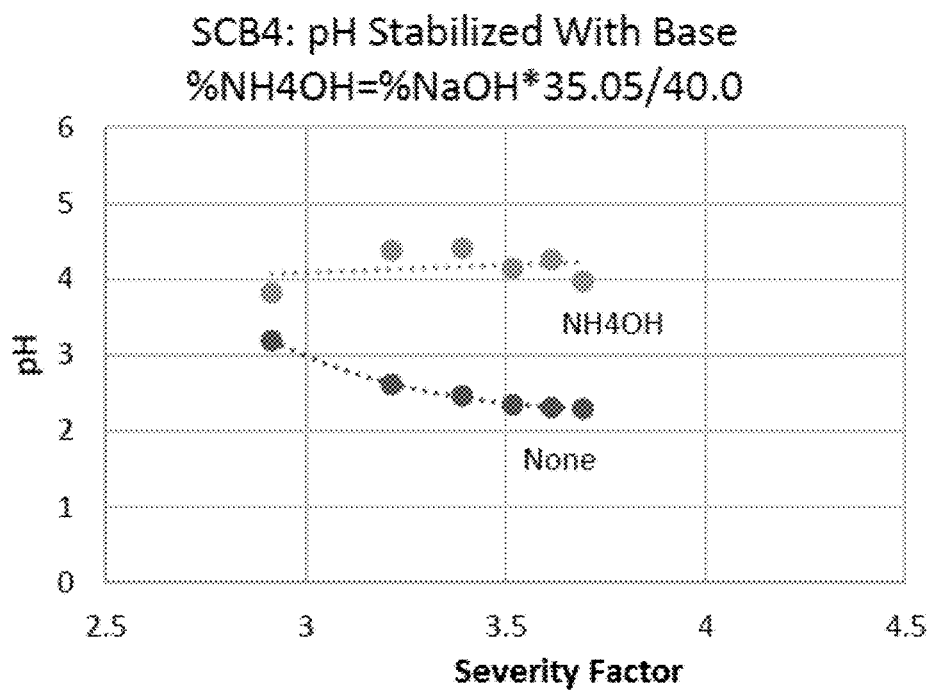
FIG. 5 is a plot showing the impact of addition of $NH_4OH$ on pH and severity factor during the treatment process.

Another test was done to compare two bases: $NH_4OH$ and NaOH and their impact on severity factor and pH. These two bases may be interchangeable governed by the formula: % $NH_4OH$=% NaOH*35.05/40.0. It was shown that, on a weight basis, $NH_4OH$ was not as effective as NaOH in preserving cellulose and hemicellulose polymers in corn stover for downstream enzymatic treatment, since more $NH_4OH$ is need than NaOH for achieving the same severity and pH in the treatment process (FIGS. 4-5).

Example 2. Oxidizing Lignin

Biomass corn stover (milled to small particles) was treated with oxygen at 165° C. for 40 min in a pH controlled treatment environment. The elemental compositions of the dried corn stover before the treatment and the dried treatment product (with soluble product washed away) are shown in Table 2. The treatment product in the measurement was the residual polymers (e.g., cellulose, hemicellulose and lignin) in the biomass. The elemental composition of dried corn stover before the treatment is presented in the column labeled "Measurements of Biomass Before Treatment," while a calculated elemental composition of corn stover based on the known components in the corn stover is presented in the column labeled "Calculated elemental composition before treatment" of Table 2. The measured and calculated elemental compositions for the corn stover were very close, indicating that the measurement method used was accurate.

The amount of oxygen in the biomass was increased from a measured level of about 40 wt. % to about 46 wt. % after the treatment, indicating that oxygen was incorporated into the biomass during the treatment.

The molar ratio of O/C of the biomass increased from 0.668 to 0.946 after the treatment (Table 2). The cellulose was not oxidized or hydrolyzed during the treatment, since theoretically cellulose is stable at a pH above 2, while the treatment had a pH above 4.5. Hemicellulose was also left unchanged, verified by saccharification and measurement of monomer sugars released, namely, glucose and xylose. Thus, cellulose and hemicellulose did not cause the change in the molar ratio of O/C. Thus, the observed increase in the molar ratio of O/C from 0.668 to 0.946 was due to lignin oxidization.

The calculated elemental composition of treatment product was calculated based on known elemental compositions for the three main components in biomass (cellulose, hemicellulose and lignin). Assuming the oxygen was not incorporated into lignin, the treatment product would have a molar ratio O/C=0.621. This was very close to the measured value of the molar ration O/C for the untreated biomass of 0.668. This confirms that a large amount of oxygen was, in fact, incorporated into lignin and that the oxygen preferentially oxidized lignin during the treatment.

Therefore, based on the measured and calculated molar ratio O/C for the biomass before and after the treatment, it was concluded that the observed large increase in the molar ratio O/C (from 0.668 to 0,946) was due to the residual "lignin" solids in the treatment product being transformed to a more highly oxygenated form, preferentially having a more acidic character, e.g. carboxylates. This was observed even though a significant portion of lignin may have been converted to solubles which were not measured, such as humates (humic acids) and fulvates (fulvic acids).

TABLE 2

Effects of Treatment on Biomass

| Elements/ Ratio | Measured elemental composition before treatment | Calculated elemental composition before treatment | Measured elemental composition of treatment product | Calculated elemental composition of treatment product |
|---|---|---|---|---|
| % Ash | 7.30 | 7.30 | 11.48 | 11.48 |
| % S | 0.06 | | 0 | |
| % C | 45.80 | 50.02 | 36.51 | 44.52 |
| % H | 5.38 | 5.68 | 5.52 | 5.31 |
| % N | 0.64 | | 0.41 | |
| % O (calc) | 40.81 | 37.50 | 46.07 | 36.88 |
| Sum | 100.0 | 100.5 | 100.1 | 98.2 |
| Molar O/C | 0.668 | 0.562 | 0.946 | 0.621 |
| Molar S/C | 0.0011 | | 0.0045 | |
| Molar H/C | 1.660 | | 1.305 | |
| Molar N/C | 0.016 | | 0.048 | |

Example 3. Products from Treatment of Biomass

This example varied temperatures and treatment times for treatment of corn stover, whiling maintaining a constant $O_2$ pressure and biomass composition.

In the first study, the temperature and treatment time resulted in a severity factor of 3.46, with or without adding base to control the pH in the treatment mixture (Table 3). Table 3 shows the composition of the treatment product (under the heading "Treatment results/markers") and the composition after enzymatic treatment of the treatment product (under the heading "20 mg/g enzyme loading").

Comparing the first three rows of Table 3 where a base was used to control pH and the last three rows of Table 3 where no base is added, the amount of oxygen retention, on a molar basis, relative to carbon in the biomass ("Molar O/C ret.") is not significantly different with the addition of base (0.6-2.8% vs. 1.1-2.0% in Table 3). However, the amount of xylose (hydrolyzed from hemicellulose polymers) was significantly lower when the base was added to control the pH (0.1-0.7% vs. 1.2-1.5% in Table 3), suggesting hemicellulose was preserved by the addition of base. Formic acid and $CO_2$ are downstream products of the breakdown of monomeric sugar and lignin. Formic acid was observed to be higher when the pH was controlled during treatment, but the total of formic acid and $CO_2$ was lower (4.4-4.5% vs. 3.7-6.4% in Table 3), suggesting that there was less $CO_2$ produced, when the pH was controlled by addition of base during treatment.

When the treatment products were subjected to enzymatic treatment (using a saccharification enzyme cocktail from Novozyme) in an amount of 20 mg enzymes per gram of cellulose in the biomass, the glucose production (from cellulose) was significantly higher when the pH was controlled during treatment by addition of base ("glucose cony.") in comparison with the case when no base was added in the treatment (70-80% vs. 61-67% in Table 3). Also, the amount of left over cellulose ("glucose polymer") was much higher when the pH was controlled during treatment (4-5% vs. 2-3% in Table 3), suggesting that a larger amount of cellulose was preserved when the pH was controlled by addition of base. This cellulose was enzymatically hydrolyzed to provide more glucose.

Further, the xylose production (from hemicellulose) was also higher when the pH was controlled during treatment ("xylose cony.") in comparison with when no base was added (56-64% vs. 51-60% in Table 3). Also, the amount of left over hemicellulose ("xylose polymer") is significantly higher when the pH was controlled during treatment (23-28% vs. 13-16% in Table 3). This also suggests that a larger amount of hemicellulose was preserved when the pH was controlled during treatment.

In summary, this example demonstrates that when the pH was controlled during the treatment, the cellulose and hemicellulose in the biomass were better preserved. The example also demonstrates that the formic acid and $CO_2$ produced in the process are from oxidization of lignin in the biomass.

When a high temperature and short treatment time (189° C., 2 min, with $NH_4OH$, third row in Table 3) were used, the result was a significantly higher sugar release than in the case of the comparable lower temperature processes (165° C./30' or 150° C./92', shown in the first two rows in Table 3). A glucose yield of 80% and a xylose yield of 64% were obtained at 189° C. and 2 min. This observation suggests that at least for some biomass materials, a higher temperature but shorter treatment time may be preferred.

TABLE 3

Production of Sugars from Biomass Using a Severity Factor 3.46

| All pretreatments with SF of 3.46 | Pretreatment results/markers | | | | | | 20 mg/g enzyme loading | | | |
|---|---|---|---|---|---|---|---|---|---|---|
| | Molar $O_2$/C ret. | C→ Xylose | C→ formic | C→ formic + $CO_2$ | DOC/ $CO_2$ | pH | glucose Conv. | xylose Conv. | glucose polymer | xylose polymer |
| 165 C., 30 min, base | 2.0% | 0.7% | 2.6% | N/A | N/A | 5.4 | 70% | 56% | 5% | 28% |
| 150 C., 92 min, $NH_4OH$ | 1.7% | 0.7% | 1.4% | 4.5% | 9.63 | 6.4 | 73% | 50% | 5% | 23% |
| 189 C., 2 min, $NH_4OH$ | 1.1% | 0.1% | 1.5% | 4.4% | 10.72 | 6.7 | 80% | 64% | 4% | 25% |
| 150 C., 92 min | 2.8% | 1.5% | 1.3% | 6.4% | 6.08 | 3.2 | 67% | 60% | 3% | 13% |
| 165 C., 30 min | 0.9% | 1.2% | 0.9% | 4.9% | 7.19 | 3.5 | 65% | 58% | 3% | 14% |
| 189 C., 2 min | 0.6% | 1.2% | 0.7% | 3.7% | 8.54 | 3.8 | 61% | 51% | 2% | 16% |

In the second study, a severity factor of 3.31 was used for the treatment, with the addition of $NH_4OH$ as the base for controlling pH as indicated in Table 4, which is similar to Table 3 described above. The amounts of xylose in the treatment product were low and the mounts of formic acid in the treatment product were high. The production of glucose and xylose after further enzymatic treatment by 20 mg enzymes per gram of cellulose (same as in Table 3) in the biomass was also high. This study confirmed that, when the pH was controlled during treatment, the cellulose and hemicellulose polymers in the biomass were preserved. The produced formic acid and $CO_2$ are thus from oxidization of lignin in the biomass.

TABLE 4

Production of Sugar from Biomass Using a Severity Factor 3.31
All pretreatments with SF of 3.31, with NH4OH

| Pretreatment Conditions | | Pretreatment results/markers | | | | 20 mg/g enzyme loading | |
|---|---|---|---|---|---|---|---|
| Hold Temp, C. | Hold Time, min | Molar $O_2$/C ret. | C→Xylose | C→Formic | pH | Glucose Conv. | Xylose Conv. |
| 155 | 59 | 3.4% | 0.6% | 1.9% | 5.56 | 66% | 54% |
| 165 | 30 | 2.5% | 0.0% | 1.7% | 5.23 | 61% | 48% |
| 175 | 15 | 1.7% | 0.6% | 1.4% | 4.21 | 68% | 57% |

Figure 6:
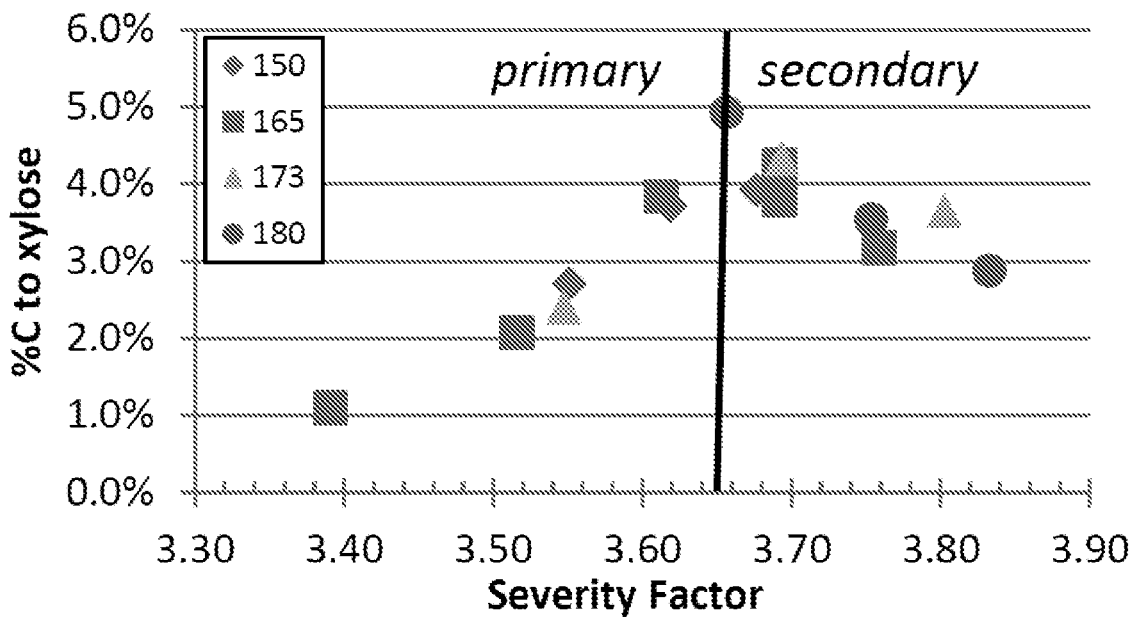
FIG. 6 is a plot showing that, as the severity factor increased, more secondary reaction products were produced by breakdown of monomer sugars.
Figure 7:
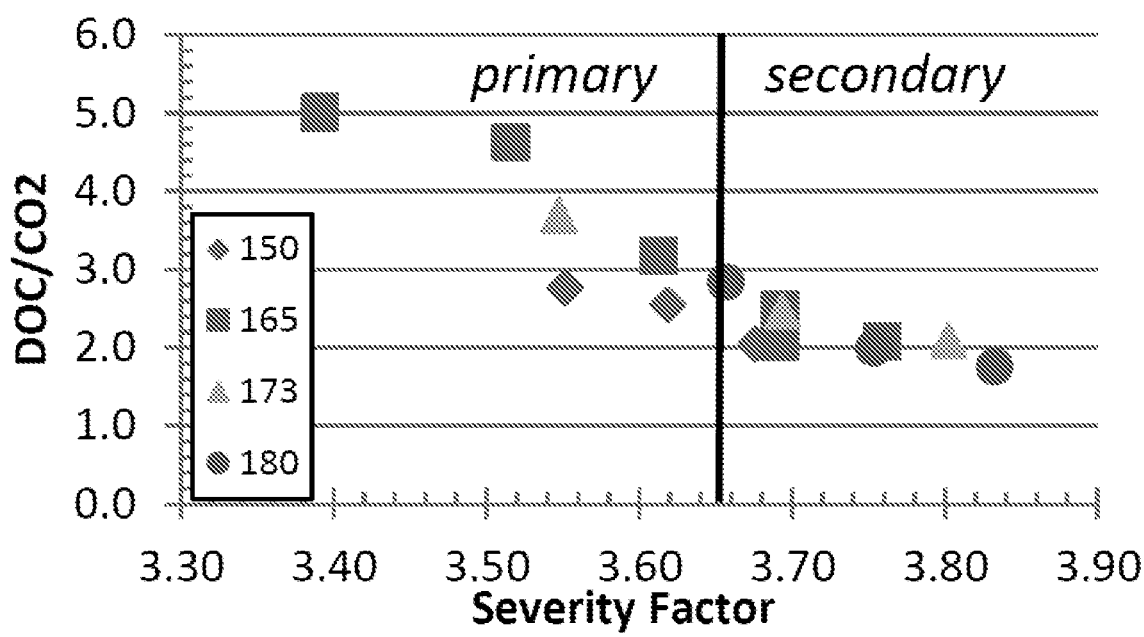
FIG. 7 is a plot showing that, as the severity factor increased, more undesirable carbon dioxide was produced, leading to waste of some of the carbon in the biomass.

In treatment process, two types of products may be produced: sugars (primary products) and oxidation products of sugars (e.g., formic acid and $CO_2$, secondary products). FIG. 6 shows the ratio of % C to xylose at different severity factors, demonstrating that as the severity factor increased, the products shift from the primary products to the secondary products, meaning more severe conditions produce more secondary products. FIG. 7 shows the ratio of DOC to $CO_2$ at different severity factors, demonstrating that as the severity factor increased, the products shifted from dissolved organic carbon to $CO_2$, meaning more severe conditions would produce more $CO_2$, resulting in a waste of carbon in the biomass.

Example 4. Addition of Iron as a Catalyst in Treatment

In this example, the corn stover was treated according to the present invention. The biomass samples were treated at two different severity factors, 3.4 and 3.6, with and without addition of $Fe^{2+}$ or $Fe^{3+}$ ions in the form of sulfates, nitrates or citrates. The sugar release after the treatment were measured (Table 5). A saccharification cocktail of enzymes comprising cellulase and hemicellulase (from Novozyme) were used in amounts of 1 or 2 wt. %, based on the total weight of cellulose in the biomass. These enzymes produce glucose from cellulose and xylose from hemicellulose ("Glucose Yield" and "Xylose Yield" in Table 5). The two columns of "Solid Glucose Yield" and "Solid Xylose Yield" show the results of direct enzymatic treatment of the same biomass without treatment.

This study shows that iron, as a free radical initiator, enhanced the rate of oxidation thereby reducing the required severity factor (e.g., by reducing treatment time) for the same product distribution of hemicellulose degradation products such as xylose.

The amount of soluble iron required to achieve this effect was very low (~80 ppm), and the iron can potentially be recycled with the water stream. After treatment, the total glucose release was enhanced in comparison to the process without treatment. However, xylose release was lowered, likely because the remaining hemicellulose in treated biomass was not as accessible.

TABLE 5

Impact of Iron as Catalyst

| Severity Factor | Iron | % Enzyme | Glucose Yield % | Xylose Yield % | Solid Glucose Yield % | Solid Xylose Yield % |
| --- | --- | --- | --- | --- | --- | --- |
| 3.6 | No Fe | 2 | 71.4% | 61.3% | 70.0% | 43.7% |
| 3.4 | Fe | 2 | 84.0% | 61.6% | 83.1% | 44.7% |
| 3.6 | No Fe | 2 | 82.8% | 69.3% | 82.0% | 59.5% |
| 3.6 | No Fe | 1 | 60.4% | 52.9% | 58.3% | 31.5% |
| 3.4 | Fe | 1 | 76.0% | 54.4% | 74.8% | 34.3% |
| 3.6 | No Fe | 1 | 73.5% | 60.9% | 72.3% | 48.5% |

It is to be understood, however, that even though numerous characteristics and advantages of the present invention have been set forth in the foregoing description, together with details of the structure and function of the invention, the disclosure is illustrative only, and changes may be made in detail, especially in matters of shape, size and arrangement of parts within the principles of the invention to the full extent indicated by the broad general meanings of the terms in which the appended claims are expressed.

All documents mentioned herein are hereby incorporated by reference in their entirety or alternatively to provide the disclosure for which they were specifically relied upon. The applicant(s) do not intend to dedicate any disclosed embodiments to the public, and to the extent any disclosed modifications or alterations may not literally fall within the scope of the claims, they are considered to be part hereof under the doctrine of equivalents.

What is claimed is:

1. A method for treating biomass, said method comprising steps of:
   (a) obtaining a mixture of the biomass, wherein the biomass comprises lignocellulosic polymers and water, wherein the water consists of inherent moisture;
   (b) treating, at a temperature in a range of from 160° C. to 200° C. for a period of from 5 seconds to 30 minutes, the mixture with at least one oxidizing agent and steam;
   (c) periodically measuring a pH of the mixture for a duration of treating step (b); and
   (d) maintaining the pH of the mixture in a range of from pH 4.5 to pH 7.0 for the duration of treating step (b) by adding a base to the mixture; and
wherein no mineral base is added to the biomass.

2. The method of claim 1, wherein the biomass comprising lignocellulosic polymers is selected from the group consisting of agricultural wastes, wood wastes and gardening wastes.

3. The method of claim 1, wherein the biomass comprising lignocellulosic polymers is selected from the group consisting of corn stover, corn cobs, palm tree empty fruit bunches, sugar cane bagasse, straw from grain crops, hay, wood waste from thinnings of deciduous and conifer forestry, sawdust from lumbering and furniture making, guayule residuals after natural rubber extraction, waste paper and cardboard.

4. The method of claim 1, wherein the at least one oxidizing agent is selected from the group consisting of air, oxygen enriched air, oxygen, ozone, perchlorates, carbon dioxide, nitrous oxide, oxides, superoxides, permanganates, chlorates, peroxides, hypochlorites and nitrates.

5. The method of claim 4, wherein the at least one oxidizing agent is selected from the group consisting of air, oxygen and oxygen enriched air.

6. The method of claim 5, wherein a weight ratio of oxygen introduced by the at least one oxidizing agent during the treating step (b) to carbon in the biomass comprising lignocellulosic polymers is in a range of from 0.2 to 1.0.

7. The method of claim 1, wherein the pH of the mixture is maintained at a pH of 5.5 to 7.0.

8. The method of claim 1, wherein the pH is measured once every second, to once every hour and the pH is measured at least 2 times during the treating step (b).

9. The method of claim 1, wherein the base is formed in situ by addition of urea to the biomass comprising the inherent moisture.

10. The method of claim 1, wherein the base is selected from the group consisting of ammonia, ammonium hydroxide and combinations thereof.

11. The method of claim 1, wherein an amount of the base added to the mixture is in a range of from 1 to 10 wt. %, based on the dry weight of the biomass comprising lignocellulosic polymers.

12. The method of claim 1, wherein an amount of the steam used in the treating step (b) is from 0.1 wt. % to 5.0 wt. % based on a dry weight of the biomass comprising lignocellulosic polymers.

13. The method of claim 1, wherein the treating step (b) is carried out at a temperature in a range of from 160° C. to 190° C.

14. The method of claim 1, wherein the treating step (b) is performed under a pressure in a range of from 201.3 KPa to 2068 KPa.

15. The method of claim 1, wherein the treating step (b) has a severity factor in a range of from 2.5 to 4.5.

16. The method of claim 1, wherein the mixture further comprises an oxidation catalyst selected from the group consisting of water insoluble metals, transition metals, precious metals, their salts or oxides, and combinations thereof.

17. The method of claim 16, wherein the oxidation catalyst comprises a metal selected from the group consisting of nickel, cobalt, platinum, palladium, rhenium, iron, copper, vanadium, zirconium and ruthenium.

18. The method of claim 1, further comprising a step of preprocessing the biomass comprising lignocellulosic polymers selected from the group consisting of grinding, milling and crushing the biomass comprising lignocellulosic polymers to reduce an average particle size of the biomass comprising lignocellulosic polymers to from 0.2 mm to 12 cm.

19. The method of claim 1, further comprising a step (e) selected from the group consisting of fermentation and enzymatic treatment using at least one enzyme selected from the group consisting of xylanases, cellulases, hemicellulases, xylosidase, esterase, arabinofuranosidase, galactanase, oxidases, peroxidases, mannases, laccases, oxidoreductases, pectinases and lipases.

20. The method of claim 19, wherein the at least one enzyme comprises at least one cellulase and at least one hemicellulase.

21. The method of claim 19, wherein step (e) comprises fermentation in a microbial digester using at least one microorganism selected from the group consisting of bacteria and fungi and the at least one enzyme is produced by a bacteria or fungus used for the fermentation.

* * * * *

UNITED STATES PATENT AND TRADEMARK OFFICE
CERTIFICATE OF CORRECTION

| | | |
|---|---|---|
| PATENT NO. | : 11,702,711 B2 | Page 1 of 1 |
| APPLICATION NO. | : 17/048512 | |
| DATED | : July 18, 2023 | |
| INVENTOR(S) | : Bartek et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 11 days.

Signed and Sealed this
Twelfth Day of November, 2024

Katherine Kelly Vidal
*Director of the United States Patent and Trademark Office*